(12) United States Patent
Ludwig et al.

(10) Patent No.: US 9,044,718 B2
(45) Date of Patent: *Jun. 2, 2015

(54) MIXING VESSEL

(75) Inventors: Jens Ludwig, Juhnde (DE);
Oscar-Werner Reif, Hannover (DE);
Gerhard Greller, Gottingen (DE);
Wolfgang Kahlert, Korle (DE); Günter Pradel, Gottingen (DE); Michael Bates, Gloucestershire (GB); Magali Barbaroux, La Destrousse (FR);
Stephanie Baud, La Bouilladisse (FR);
Isabelle Gay, Peypin (FR); Sebastien Chaussin, Aubagne (FR)

(73) Assignee: SARTORIUS STEDIM BIOTECH GMBH, Gottingen (DE)

(*) Notice: Subject to any disclaimer, the term of this patent is extended or adjusted under 35 U.S.C. 154(b) by 930 days.

This patent is subject to a terminal disclaimer.

(21) Appl. No.: 12/918,351

(22) PCT Filed: Mar. 18, 2009

(86) PCT No.: PCT/IB2009/051150
§ 371 (c)(1),
(2), (4) Date: Nov. 1, 2010

(87) PCT Pub. No.: WO2009/116002
PCT Pub. Date: Sep. 24, 2009

(65) Prior Publication Data
US 2011/0038222 A1    Feb. 17, 2011

Related U.S. Application Data

(60) Provisional application No. 61/069,977, filed on Mar. 19, 2008.

(51) Int. Cl.
*B01F 3/04* (2006.01)
*B01F 7/00* (2006.01)
(Continued)

(52) U.S. Cl.
CPC ......... *B01F 3/04269* (2013.01); *B01F 7/00633* (2013.01); *B01F 7/00691* (2013.01);
(Continued)

(58) Field of Classification Search
CPC ............. B01F 3/04269; B01F 7/00633; B01F 7/00691; B01F 7/1695; B01F 7/22; B01F 13/0827; B01F 15/00071; B01F 15/00396; B01F 15/00707; B01F 15/00831; B01F 15/0085; B01F 15/065; C12M 23/26; C12M 27/02; C12M 29/06
USPC ....................................... 435/289.1
See application file for complete search history.

(56) References Cited

U.S. PATENT DOCUMENTS

| 3,625,834 A | 12/1971 | Muller |
| 4,209,259 A | 6/1980 | Rains et al. |

(Continued)

FOREIGN PATENT DOCUMENTS

| EP | 1 884 561 A1 | 2/2008 |
| EP | 2 039 754 A1 | 3/2009 |

(Continued)

OTHER PUBLICATIONS

International Search Report, dated Jul. 16, 2009, from corresponding PCT application.

*Primary Examiner* — Nathan Bowers
*Assistant Examiner* — Gautam Prakash
(74) *Attorney, Agent, or Firm* — Young & Thompson

(57) ABSTRACT

A mixing vessel includes a flexible container, elements for mixing its contents, aeration elements, a drain/lower bearing port having a rigid flange provided with a drain passage, attached in a tight manner to the lower portion of the container wall, supporting a lower bearing that is adjacent to the drain passage. The vessel includes an extended element for dispensing aeration gas and is spaced essentially radially from the drain/bearing port; at least one tubular element for dispensing aeration gas extends from the extended dispensing element, in the inside space, along the inside surface of the lower portion and the side portion of the wall of the container and extends on the outside of the container from the upper portion; at least one mixing element is spaced essentially from the lower portion of the container wall, from the lower bearing, and from at least one extended element for dispensing aeration gas.

38 Claims, 12 Drawing Sheets

(51) Int. Cl.
  *B01F 7/16* (2006.01)
  *B01F 7/22* (2006.01)
  *B01F 13/08* (2006.01)
  *B01F 15/00* (2006.01)
  *B01F 15/06* (2006.01)
  *C12M 1/00* (2006.01)
  *C12M 1/06* (2006.01)

(52) U.S. Cl.
  CPC .............. *B01F 7/1695* (2013.01); *B01F 7/22* (2013.01); *B01F 13/0827* (2013.01); *B01F 15/00071* (2013.01); *B01F 15/00396* (2013.01); *B01F 15/00707* (2013.01); *B01F 15/00831* (2013.01); *B01F 15/0085* (2013.01); *B01F 15/065* (2013.01); *C12M 23/26* (2013.01); *C12M 27/02* (2013.01); *C12M 29/06* (2013.01); *B01F 15/00123* (2013.01); *B01F 2003/04326* (2013.01); *B01F 2003/04361* (2013.01); *B01F 2003/04879* (2013.01); *B01F 2003/04893* (2013.01); *B01F 2015/062* (2013.01); *B01F 2215/0073* (2013.01)

(56) References Cited

U.S. PATENT DOCUMENTS

| | | |
|---|---|---|
| 4,670,397 A | 6/1987 | Wegner et al. |
| 4,960,706 A | 10/1990 | Bliem et al. |
| 4,993,841 A | 2/1991 | Lofgren et al. |
| 5,206,172 A | 4/1993 | Uchihori et al. |
| 5,470,152 A | 11/1995 | Rains |
| 5,795,732 A | 8/1998 | Schilling et al. |
| 7,384,783 B2 * | 6/2008 | Kunas et al. ............... 435/289.1 |
| 2006/0270036 A1 | 11/2006 | Goodwin et al. |
| 2008/0139865 A1 * | 6/2008 | Galliher et al. ............. 588/249 |
| 2009/0142827 A1 | 6/2009 | Schoeb |

FOREIGN PATENT DOCUMENTS

| | | |
|---|---|---|
| EP | 2 065 085 A1 | 6/2009 |
| GB | 1 519 526 A | 8/1978 |
| JP | 56-045752 A | 4/1981 |
| WO | 03/028869 A2 | 4/2003 |
| WO | 2008/088371 A2 | 7/2008 |

* cited by examiner

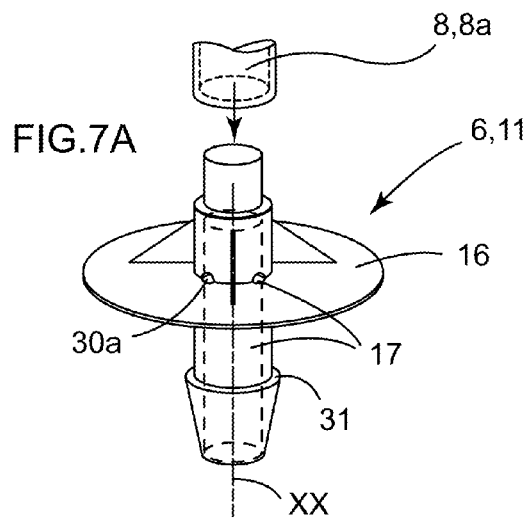
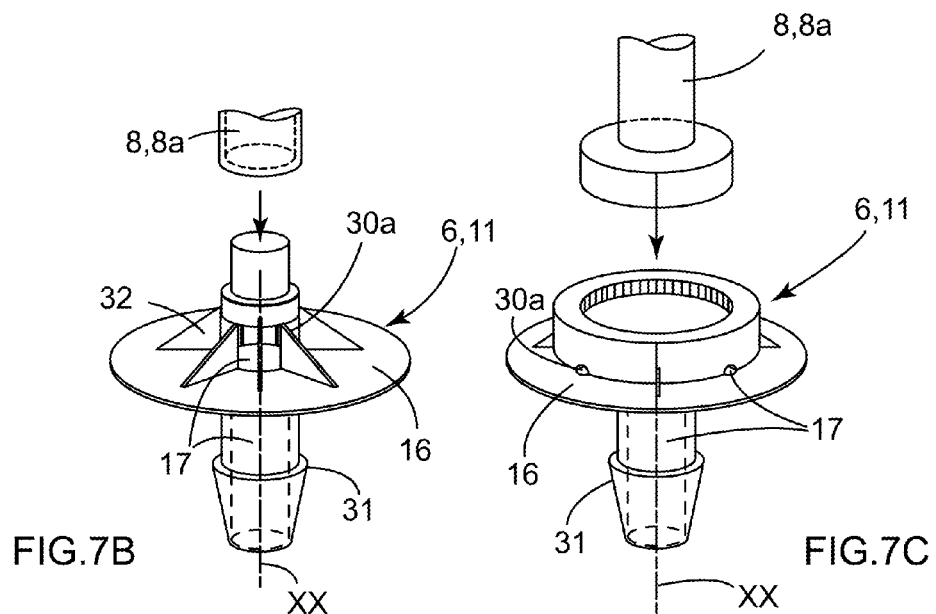

MIXING VESSEL

BACKGROUND OF THE INVENTION

The invention relates to the field of mixing vessels.

Description of the Related Art

Its purpose more particularly is a mixing vessel that is designed to receive biopharmaceutical contents for the purpose of the mixing thereof, such a mixing vessel acting as a bioreactor, and a process for using such a mixing vessel.

Mixing tanks or tanks with stirring mechanisms comprising a rotary stirring apparatus are generally used for mixing chemical compounds. The ingredients that are mixed in tanks with stirring mechanisms frequently require a sterile environment, such as when the ingredients are mixed for preparing a pharmaceutical product. Although certain applications do not require a sterile environment, the Food and Drug Administration of the USA published strict sterility requirements for certain solutions. To ensure a sterile environment of this type, the mixing tanks should be built to prevent contaminants from entering inside during the entire batch process, including during the filling, the mixing and the draining of the tanks.

The use of magnetic feeds for driving the stirring apparatus has become more common since these feeds do not require any physical connection or attachments between the moving parts of the driving means and the stirring apparatus in the sterile environment. In the tanks with stirring mechanisms that are suitable for the stirring apparatus driven magnetically, the latter, arranged inside the tank, comprises a magnetic element that is close to the bottom of the tank with a stirring mechanism, which is actuated by a corresponding magnetic element that is arranged on a drive motor on the outside of the tank. The activation of the drive motor that has the corresponding magnetic element positioned close to the magnetic element of the stirring apparatus drives the rotation of the latter inside the tank with the stirring mechanism.

Even more recently, tanks with sterile stirring mechanisms have been developed to use a flexible vessel as a mixing container. The flexible vessels can be built in a sterile environment and sealed hermetically before use. These systems, which use a tank support for maintaining the integrity of the flexible container when it is filled, are generally thrown away after use to eliminate the need for cleaning so as to recreate a sterile environment in the vessel between uses. The capacity for monitoring the sterile environment is therefore greatly improved.

In addition, it is known that the tanks with stirring mechanisms that are designed to be used in sterile applications comprise the stirring apparatus in the vessel that is sealed hermetically during shipping. In these tanks with stirring mechanisms, the sterile stirring apparatus is arranged inside the sterile vessel before hermetic sealing, reducing the risk of breaching the sterile environment.

Examples of tanks with stirring mechanisms that comprise a stirring apparatus with internal fluid driven magnetically are presented in the documents U.S. Pat. No. 4,209,259, U.S. Pat. No. 4,993,841, U.S. Pat. No. 5,470,152, JP-A-56-045752 and WO PCT/US02/31478. Each of its references describes tanks with stirring mechanisms comprising a stirring apparatus having driven magnetic elements that are activated by adjacent, cooperating magnetic drive elements combined with a driving means.

Among the references cited, the document U.S. Pat. No. 5,470,152 describes a tank with a stirring mechanism that comprises a drive housing into which the drive element is inserted. A rotor that has a magnetic element is attached to the drive housing, whereby the magnetic element comprises magnets that are oriented vertically, so as to be parallel to the longitudinal axis of the drive housing that contains the cooperating magnetic element. As illustrated and described in the reference, the rotor is attached in a removable manner to the lower portion of the drive housing by a clamp.

The documents U.S. Pat. No. 4,209,259 and U.S. Pat. No. 4,993,841 describe mixing vessels with a stirring apparatus that is driven magnetically in the form of rotors mounted on struts in the vessels. Each of these references describes the stirring apparatus as being located inside the vessel, in a region that is close to a flange or a housing that positions the rotor relative to the driving means. The rotors of these references are located, however, in the vessel in its sole position on a strut and can be withdrawn by pulling on a ring that is arranged at the terminal end of the stirring apparatus.

In a similar manner, the device of the document WO PCT/US02/31478 uses a rotor that is received by a strut that is arranged on a rigid portion of the mixing vessel. The remaining portion of the mixing vessel is designated as being a flexible portion, described in the reference as a bag. The rotor comprises a magnetic element that is driven by an external drive motor that has a magnetic drive element.

The document JP-A-56-045752 relates to a stirring device that is driven magnetically and that has a rotary circular plate on ball bearings attached to the lower portion of the vessel, where the magnetic element of the stirring apparatus is combined with the lower portion of the vessel. The stirring apparatus of this reference is formed by a metal alloy that is designed to be used up.

None of the references of the prior art describes, however, a disposable mixing vessel that is sealed hermetically and is sterile, comprising a fixed central axis with upper and lower portions of the vessel and using stop bearings or radial bearings, such as plain bearings, ball bearings, or roller bearings to facilitate the rotation of the shaft, on which one or more rotor(s) is (are) mounted. In addition, none of the references describes a disposable mixing vessel that has a drain opening incorporated in the lower attachment element of the shaft to empty the vessel once the mixing process is implemented.

Furthermore, the document US-A-2006/0270036 describes a mixing vessel that, in one embodiment, comprises:

An external rigid holding device comprising a bottom wall, a peripheral wall, and an upper opening, delimiting a housing, A flexible container that is arranged in the housing, comprising:
  A wall that has a lower portion, a side portion and an upper portion, delimiting an inside space designed to receive a certain amount of the contents,
  Ports for introducing components of the contents into the container and for drainage of the contents formed in the upper portion of the wall of the container, Means for mixing the contents, comprising a straightened shaft, arranged, on the one hand, to be driven in rotation by mechanical motor means integrally arranged on the outside of the container, and, on the other hand, to drive in rotation a mixing disk with flexible flaps, located in the inside space, in the immediate vicinity of the lower portion of the wall of the container, mounted so as to be able to rise or descend, Aeration means arranged to deliver to the contents a certain amount of aeration gas, comprising, on the one hand, aeration gas intake means having a tubular element that passes through the lower portion of the wall of the container between the inside space and the outside, and, on the other hand, in fluid communication, means for dispensing aeration gas comprising a dispensing element that has a transverse straight cross-section in a ∩ shape with divergent branches, whose wall allows the passage of the bubbles of aeration gas coming from the intake means, located in the inside space by adjoining the lower portion of the wall of the container and immediately below the mixing disk.

Such a mixing vessel has several drawbacks. The mixing disk is located toward the lower portion of the container, which limits the mixing achieved and proves particularly unsuitable in the case where it is desired to have a large-capacity container, for example able to reach 5,000 liters. The drawback is all the more real since the aeration gas dispensing element is confined between the lower portion of the wall of the container and the mixing disk.

The document WO 2008/088371 describes a mixing vessel of the same general type and consequently having the same drawbacks.

The document U.S. Pat. No. 5,206,172 describes a fermentation vessel that comprises means for dispensing aeration gas in toric form. Such a vessel corresponds to a well-defined usage, and it does not provide the presence and the implementation of the mixing means.

SUMMARY OF THE INVENTION

The purpose of the invention is to solve the problems posed by the known mixing vessels of the type comprising aeration means, and, more particularly, to optimize the mixing as well as the aeration, including the case of large-capacity containers, for example containers that can reach 5,000 liters.

For this purpose, according to a first aspect, the object of the invention is a mixing vessel that is designed to receive biopharmaceutical contents for the purpose of the mixing thereof, comprising:
  A flexible container, comprising:
    A wall that has a lower portion, a side portion, and an upper portion, delimiting an inside space able to receive a certain amount of contents,
    One or more ports for introducing contents or components of contents into the container, working with one or more introduction openings made in the container,
    At least one drain port of the contents working with at least one drain opening,
  Means for mixing the contents, comprising:
    At least one straightened shaft, able to be driven in rotation by motor means and to drive in rotation at least one mixing element,
    At least one lower bearing, adjacent to the lower portion of the wall of the container, with which the lower portion of the shaft works,
    At least one mixing element, able to stir the contents, located in the inside space,
  Aeration means able to deliver a certain amount of aeration gas to the contents, comprising:
    Aeration gas intake means having at least one tubular element that extends in fluid communication from the outside of the container to the dispensing means,
    Means for dispensing aeration gas comprising at least one extended dispensing element whose wall allows the passage of the bubbles of aeration gas coming from the intake means, located in the inside space toward the lower portion of the wall of the container, characterized by the fact that:
  It comprises at least one combined drain/lower bearing port that has a rigid flange:
    Provided with a drain passage in fluid communication on one side with the inside space and on the other side with the outside of the container,
    Attached in a rigid and tight manner to the lower portion of the wall of the container around the drain opening, whereby the drain passage and the drain opening are in fluid communication,
    Supporting on the inside a lower bearing located in the inside space, adjacent to the drain passage without preventing the fluid communication between the drain passage and the drain opening,
  The at least one extended element for dispensing aeration gas is spaced essentially radially from the drain/bearing port,
  The at least one tubular aeration gas intake element extends from the extended dispensing element in the inside space, along the inside surface of the lower portion and the side portion of the wall of the container and extends to the outside of the container from—or from the vicinity of—the upper portion of the wall of the container;
  At least one mixing element is spaced essentially from the lower portion of the wall of the container, from the lower bearing, and from at least one extended element for dispensing aeration gas,
such that the bubbles from the aeration gas that are dispensed from the at least one extended element for dispensing aeration gas are distributed in the contents by a first distribution in the lower region of the inside space that is adjacent to the lower portion of the wall of the container, by the at least one extended element for dispensing distribution gas and a second distribution by the at least one mixing element in the entire inside space of the container.

According to a first embodiment, the at least one shaft of the mixing means works with a single bearing—the lower bearing—whereby the drive motor means with rotation of the shaft is located toward the lower portion of the wall of the container.

According to a second embodiment, the at least one shaft of the mixing means works with two bearings, its lower portion with the lower bearing and its upper portion with an upper bearing that is adjacent to the upper portion.

According to one embodiment, the mixing vessel comprises at least one upper bearing that has a rigid flange that is attached rigidly to the upper portion of the wall of the container, supporting from the inside an upper bearing that is located in the lower space.

According to one embodiment, the mixing vessel comprises at least one combined introduction/upper bearing port that has a rigid flask:
  Provided with a passage for introducing the contents or the components of the contents in fluid communication on one side with the lower space, and on the other side with the outside of the container,
  Attached in a rigid and tight manner to the upper portion of the wall of the container around the introduction opening, whereby the introduction passage and the introduction opening are in fluid communication,
  Supporting from the inside the upper bearing that is located in the inside space, adjacent to the introduction passage without preventing the fluid communication between the introduction passage and the introduction opening.

According to the embodiments, the drive motor means with rotation of the shaft is located toward the upper portion and/or toward the lower portion of the wall of the container.

According to a first embodiment, the at least one shaft of the mixing means is located in its entirety in the inside space, whereby the drive motor means with rotation of the shaft operates magnetically, a rotary disk driving with magnetic poles, located on the outside of the container, operationally working with a rotary disk driven with magnetic poles, attached to at least one shaft with magnetic proximity of the driving rotary disk.

According to a second embodiment, the at least one shaft of the mixing means is partially located in the inside space and partially on the outside of the container, whereby the drive motor means with rotation of the shaft operates mechanically, with a driving rotary shaft, located on the outside of the container, operationally working with the outside portion of the at least one shaft.

According to a first embodiment, the mixing means comprise a single straightened shaft. According to a second embodiment, the mixing means comprise several straightened shafts with essentially parallel shafts, each able to drive in rotation at least one mixing element.

According to a first embodiment, a shaft of the mixing means supports and drives a single mixing element that is located at a single axial location on the shaft. According to a second embodiment, a shaft of the mixing means supports and drives several mixing elements that are located at a large number of axial locations on the shaft.

According to one embodiment, a mixing element is spaced essentially from the lower portion of the wall of the container, from the lower bearing, and from the at least one extended dispensing element, from a distance on the order of at least one-quarter of the spacing between the lower portion and the upper portion of the wall of the container.

According to one embodiment, a mixing element is spaced essentially from the lower portion of the wall of the container, from the lower bearing and from the at least one extended dispensing element, from a distance on the order of at least one-third of the spacing between the lower portion and the upper portion of the wall of the container.

According to one embodiment, the at least one tubular aeration gas intake element extends into the inside space by being kept essentially adjoining or adjacent to the inside surface of the wall of the container.

According to the embodiments, the at least one tubular aeration gas intake element is at least partially structurally separate from the wall of the container and held to it by gluing, welding or by means of connected holding parts and/or at least partially structurally an integral part of the wall of the container.

According to one embodiment, the at least one tubular aeration gas intake element passes through the wall of the container by a tight connection.

According to one embodiment, the at least one tubular aeration gas intake element passes through the wall of the container into the upper portion.

According to one embodiment, the at least one extended element for dispensing aeration gas is kept adjoining or adjacent to the inside surface of the lower portion of the wall of the container.

According to the embodiments, the at least one extended element for dispensing aeration gas is, at least partially, structurally separate from the wall of the container and held to it by gluing, welding, or by connected holding parts and/or at least partially structurally an integral part of the wall of the container.

According to one embodiment, the at least one extended element for dispensing aeration gas does not pass through the wall of the container.

According to one embodiment, the at least one extended element for dispensing aeration gas comprises a wall that is provided with a large number of distributed holes that can allow the passage of the bubbles of aeration gas coming from the intake means.

According to one embodiment, the large number of holes that can allow the passage of the bubbles of aeration gas coming from the intake means are oriented with different axes of inclination with respect to the vertical line.

According to the embodiments, the holes of the large number of holes are either the same size or are different sizes.

According to one embodiment, the at least one extended element for dispensing aeration gas has, in a transverse straight cross-section, a circular or pseudo-circular or elliptical or pseudo-elliptical shape.

According to a first embodiment, the at least one extended element for dispensing aeration gas comprises at least one complete ring that is closed on itself in a circular communication that may or may not be continuous. According to a second embodiment, the at least one extended element for dispensing aeration gas comprises at least one incomplete ring that is open relative to itself. In this case, and according to one embodiment, the incomplete ring has an angular opening of between about 180° and 270°.

According to one embodiment, the at least one extended element for dispensing aeration gas comprises at least one ring and at least one transverse element in fluid communication.

According to one embodiment, the at least one ring of at least one extended element for dispensing aeration gas is essentially centered on the combined drain/bearing port.

According to a first embodiment, the aeration means comprise a single unit of aeration gas intake means and means for dispensing aeration gas. According to a second embodiment, the aeration means comprise several distinct units of intake means of one or more aeration gases and means for dispensing the aeration gas(es).

According to the embodiments, a unit of aeration means comprises a single tubular aeration gas intake element that communicates with a single extended element for dispensing aeration gas, or a single tubular aeration gas intake element that communicates with several extended elements for dispensing aeration gas, or several tubular aeration gas intake elements that communicate with a single extended element for dispensing aeration gas, or several tubular aeration gas intake elements that communicate with several extended elements for dispensing aeration gas.

According to one embodiment, in the case where the mixing vessel comprises several separate extended elements for dispensing aeration gas, at least some of the several extended elements for dispensing aeration gas are located in a large number of radial locations in the inside space toward the lower portion of the container.

According to one embodiment, the several separate extended elements for dispensing aeration gas are spaced essentially radially from the drain/bearing port up to the vicinity of the side portion of the wall of the container.

According to one embodiment, an extended element for dispensing aeration gas is spaced essentially radially from the drain/bearing port, from a distance on the order of at least one-fifth of the diameter of the lower portion of the wall of the container.

According to one embodiment, only the drain projects under the lower portion of the wall of the container and, if necessary, the drive motor means of the mixing means when it is provided in the lower portion.

According to one embodiment, the mixing vessel also comprises one or more gas drain ports working with at least one drain opening that is made in the upper portion of the wall of the container, provided with a non-return valve, preventing the introduction into the container of fluids or contaminants that are not desired or are undesirable.

According to one embodiment, the mixing vessel also comprises one or more ports for introduction, drainage, and assembly.

According to one embodiment, the container has a large capacity and can range up to 5,000 liters.

According to one embodiment, the mixing vessel also comprises an external rigid holding device of the container that is filled with its contents, comprising a bottom wall, a peripheral wall, and an upper opening, delimiting a primary housing in which the flexible container, whose inside portion rests on the bottom wall and whose side portion is applied, when the container is filled with its contents, against the peripheral wall, is arranged in a removable manner.

In this case and according to one embodiment, the external rigid holding device also comprises a secondary housing below the bottom wall for housing and for protection of the drainage and, if necessary, the drive motor means of the mixing means when it is provided in the lower portion.

According to one embodiment, the external rigid holding device also comprises heating means, and the flexible container is made of a material that has a certain thermal conductivity such that the implementation of the heating means makes it possible to heat the contents, and, if necessary, means for monitoring the temperature of the container and means for controlling the heating means.

According to one characteristic, the container can be found in three extreme states: a disassembled state of the external rigid holding device in which the container can be arranged flattened on itself, an assembled state of the external rigid holding device in which the container, empty of contents, is arranged in the primary housing of the holding device by resting on the bottom wall, and an assembled state of the external rigid holding device in which the container, filled with its contents, is arranged in the primary housing of the holding device by resting on the bottom wall and by being applied against the peripheral wall.

According to a particular embodiment of the mixing vessel, a bioreaction is produced there, whereby the mixing vessel is a bioreactor.

According to a second aspect, the object of the invention is a process for implementing a mixing vessel as was just described, in which:
  Such a mixing vessel whose drain port is sealed is available,
  The contents or the components of the contents designed to be received in the container of the mixing vessel and then mixed are available,
  The contents or the components of the contents are introduced into the container,
  The mixing means are used to stir the contents of the container,
  The aeration means are used to deliver to the container a certain amount of aeration gas, aeration and the mixing being carried out at least partially simultaneously, and
  The aeration gas bubbles are dispensed from the at least one extended element for dispensing aeration gas, and they are distributed into the contents for a first distribution in the lower region of the inside space that is adjacent to the lower portion of the wall of the container by the at least one extended element for dispensing aeration gas and a second distribution by the at least one mixing element in the entire inside space of the container.

According to one embodiment, a component or a portion of the components of the contents is/are first introduced into the container, the mixing means and the aeration means are implemented, and a certain amount of aeration gas is introduced to be delivered to the contents, and the remaining component(s) of the contents is/are introduced into the container.

According to one embodiment:
  A start is made from a mixing vessel whose container is disassembled from an external rigid holding device, empty of contents, and arranged flattened upon itself,
  The container is assembled with the external rigid holding device by arranging it in the primary housing of the latter and by resting on its bottom wall,
  The contents or components of the contents are then introduced into the container.

According to one embodiment, the drain and the drive motor means of the mixing means are arranged under the lower portion of the wall of the container when it is provided in the lower portion.

BRIEF DESCRIPTION OF THE DRAWING FIGURES

Several embodiments of the invention will now be described using drawings in which:

FIGS. 7A, 7B and 7C are three perspective views of three embodiments of a combined drain/bearing port designed to be part of the mixing vessel.

DETAILED DESCRIPTION OF THE INVENTION

Figure 1:
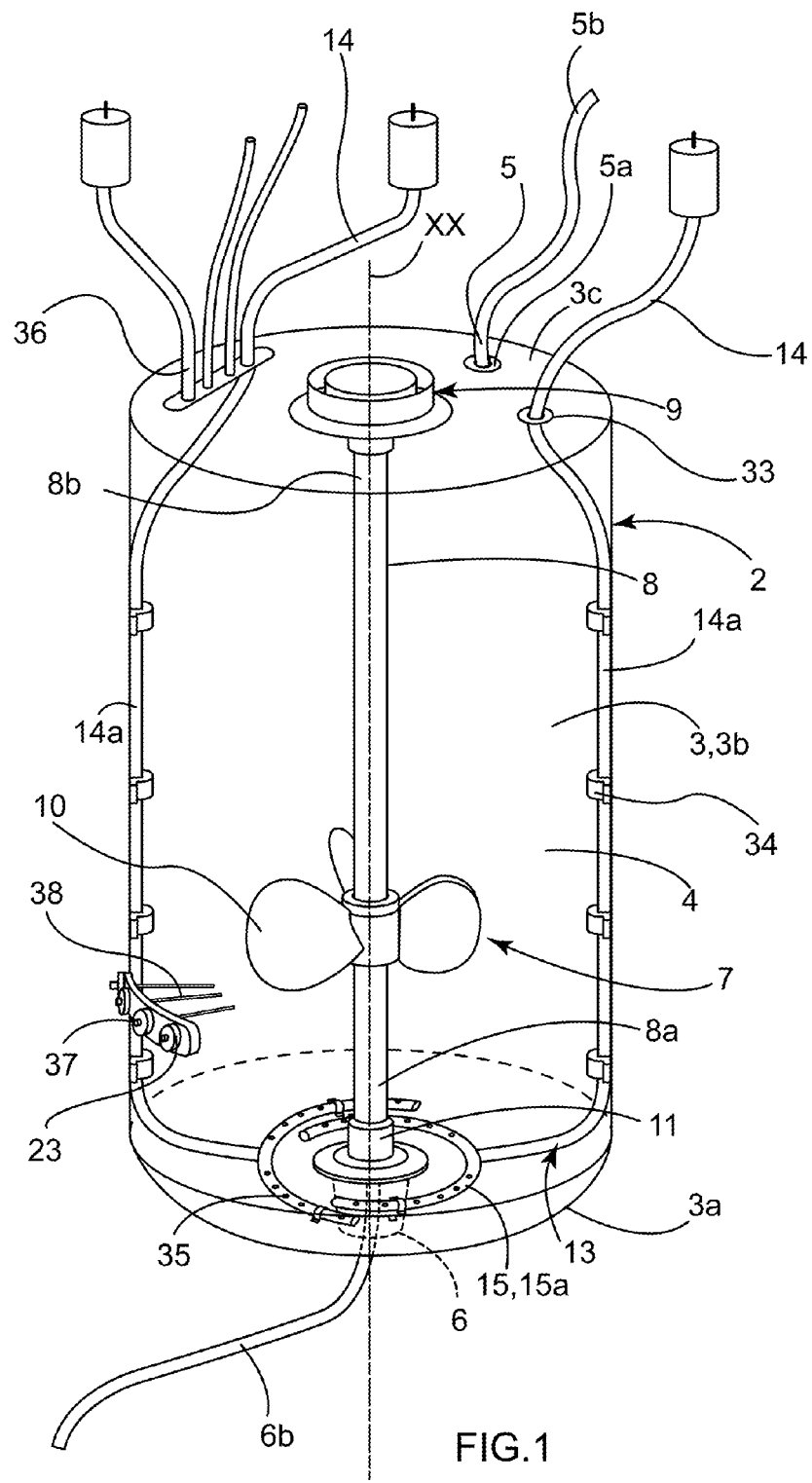
FIG. 1 is a perspective view of a possible embodiment of a mixing vessel whose external rigid holding device is not shown.

A mixing vessel 1 according to the invention is designed to receive biopharmaceutical contents C for the purpose of the mixing thereof or, if necessary, for the purpose of a bioreaction, the mixing vessel 1 then being a bioreactor.

The contents C comprise one or at least one liquid phase. If necessary, the contents C are produced from several components $C_1, C_2, \ldots$ of which at least one is in the liquid phase and of which one or more can be in the solid phase, such as powder. If necessary, in the case of a bioreactor, the contents C also comprise cells, micro-organisms, . . . .

The mixing vessel 1 has a primary XX axis that is vertical.

The mixing vessel 1 first comprises a flexible container 2. This flexible container 2 is formed by a wall 3 made of one or more sections that are made integral with one another, having a lower portion 3a, a side portion 3b, and an upper portion 3c, delimiting an inside space 4 that can receive a certain amount of the contents C.

According to one embodiment, the flexible container 2 is disposable.

The flexible container 2 can have a capacity that ranges up to 5,000 liters based on requirements and applications.

The words "vertical," "horizontal," "upper," and "lower" refer to the situation in which the mixing vessel 1 is in a position that is capable of its operation. It is understood, however, that the mixing vessel 1 can occupy other positions or have other states, for example because it is not in operation. The word "vertical" is not to be included in a narrow sense, but in the sense meaning from higher to lower and vice versa.

In contrast, the words "inside" and "outside" refer respectively to what is located inside and outside of the container 2.

Finally, the words "axial," on the one hand, and "radial" and "transverse," on the other hand, refer to that which extends in or parallel or essentially parallel to the XX axis, on the one hand, and perpendicularly or orthogonally or essentially perpendicularly or orthogonally to the XX axis, on the other hand.

The mixing vessel 1 comprises one or more through ports 5 for introducing the contents C or components $C_1, C_2, \ldots$ of contents C into the container 2, working with one or more introduction openings 5a made in the container 2.

The mixing vessel 1 also comprises at least one through port 6 for draining the contents C from the container 2, working with at least one drain opening 6a made in the container 2. Naturally, the drain port 6 is able to be sealed each time as necessary and in contrast can be open for draining.

In this document, "port" is defined as a connecting means or physical connection. Such a port is a through port when it involves ensuring a linking function between the inside and the outside of the container 2, for example for the introduction or the drainage of what is to be arranged or is arranged in the container 2. Such a port can also be a non-through port when it involves ensuring a holding function of an element of the mixing vessel.

Pipes, pockets, and tanks 5b, if necessary flexible ones, can be associated with the ports 5, in fluid communication and with a tight—and, if necessary, removable—connection. Likewise, pipes, pockets, and tanks 6b, if necessary flexible ones, can be associated with ports 6, in fluid communication and with a tight—and, if necessary, removable—connection. These pipes, pockets, and tanks 5b and 6b are located and extend on the outside of the mixing vessel 1 and are connected in a proper manner to intakes and drains, respectively. These pipes, pockets, and tanks 5b, 6b are adapted—in particular regarding their size—to the nature of what they contain or ensure the passage. The tight—and, if necessary, removable—connection is ensured by any suitable device, as it is known in the field of the invention.

In the embodiment shown in FIG. 1, the introduction ports 5 are arranged in the upper position of the mixing vessel 1, and the introduction openings 5a are made in the upper portion 3c of the wall 3, while the drain port 6 is arranged in the lowest position of the mixing vessel 1, and the drain opening 6a made in the lower portion 3a of the container 2 is arranged in its lowest region. If necessary, one (or more) introduction port(s) 5 is/are arranged in the lower position of the mixing vessel 1, and the corresponding introduction opening 5a is made in the lower portion 3a of the container 2 or in the lower region of the side portion 3b.

The mixing vessel 1 also comprises means 7 for mixing the contents of the container 2. Mixture means that which is located in the inside space 4 of the container 2, whether it is the contents C, or a portion of its components, and/or only a portion of the total amount that is to be arranged there.

First, the mixing means 7 comprise at least one straightened shaft 8, able to be driven in rotation by motor means 9 and to drive in rotation at least one mixing element 10.

Second, the mixing means 7 comprise at least one lower bearing 11, adjacent to the lower portion 3a of the wall 3, with which the lower portion 8a of the shaft 8 works.

Third, the mixing means 7 comprise at least one mixing element 10, able to stir the contents, located in the inside space 4.

The mixing vessel 1 also comprises aeration means 13 that can deliver a certain amount of aeration gas to the contents. Aeration means that which is located in the inside space 4 of the container 2, whether it is the contents C or a portion of its components and/or only a portion of the total amount that is to be arranged there.

First, the aeration means 13 comprise aeration gas intake means 14 that have at least one tubular element 14a that extends with fluid communication from the outside of the container 2 to the dispensing means 15.

Second, the aeration means 13 comprise the aeration gas dispensing means 15 that comprise at least one extended dispensing element 15a whose wall allows the passage of the bubbles of aeration gas coming from the intake means 14. This extended element 15a for dispensing aeration gas is located in the inside space 4, toward the lower portion 3a of the wall 3 of the container 2.

The mixing vessel 1 also comprises at least one combined drain/lower bearing port 6+11 that has a rigid flange 16.

"Flange" is defined here as a rigid part in the general shape of a solid wall, at least essentially flat, arranged flat, and designed for holding.

First, the flange 16 is provided with a drain passage 17. This passage 17 is in fluid communication on one side with the inside space 4 of the container 2, and on the other side with the outside of the container 2. Thus, the draining of the contents of the container 2 to the outside of the mixing vessel is possible.

Second, the flange 16 is attached in a rigid and tight manner to the lower portion 3a of the wall 3 of the container 2, around the drain opening 6a. The drain passage 17 and the drain opening 6a are in fluid communication.

Third, the flange 16 supports, from the inside, the lower bearing 11, which is located in the inside space 4 and is adjacent to the drain passage 17, without preventing the fluid communication between the drain passage and the drain opening.

Furthermore, the at least one extended element 15a for dispensing aeration gas is spaced essentially radially from the drain/bearing port 6+11. Extended element 15a means that said element is not incorporated in or in the immediate proximity of the drain/bearing port 6+11.

The at least one tubular aeration gas intake element 14a extends from the extended dispensing element 15a in the inside space 4 along the inside surface of the lower portion 3a and the side portion 3b of the wall 3 of the container 2. The at least one tubular aeration gas intake element 14a extends to the outside of the container 2 from—or from the vicinity of—the upper portion 3c of the wall 3 of the container 2.

At least one mixing element 10 is spaced essentially from the lower portion 3a of the wall 3 of the container 2, from the lower bearing 11, and from at least one extended element 15a for dispensing aeration gas. The meaning of this is that the mixing element 10 is not incorporated into or in the immediate vicinity of the wall 3 of the container 2, of the lower bearing 11, and of at least one extended element 15a for dispensing aeration gas.

The preceding structural arrangements are such that the bubbles of aeration gas that are dispensed from the at least one extended element 15a for dispensing aeration gas are distributed in the contents of the inside space 4 by, on the one hand, a first distribution in the lower region of the inside space 4 that is adjacent to the lower portion 3a of the wall 3 of the container 2, by the at least one extended element 15a for dispensing distribution gas, and, on the other hand, a second distribution by the at least one mixing element 10 in the entire inside space 4 of the container 2.

Because of the flexible nature of the container 2, the mixing vessel 1 also comprises an external rigid—optionally semi-rigid—holding device 18 of the container 2 that is filled with its contents during the filling, the mixing, and the draining.

The external rigid holding device 18 comprises a bottom wall 19 and a peripheral wall 20, forming an upper access opening 21 and delimiting a primary housing in which the flexible container 2 is arranged in a removable manner.

The external rigid holding device 18 generally has the geometry, shape and/or dimension that is identical to the flexible container 2, so as to reduce the stresses on the welds or the changes in direction in the material of the flexible container 2.

The external rigid holding device 18 comprises the access opening 21 so as to allow the installation and the removal of the flexible container 2.

If necessary, the external rigid holding device 18 comprises other openings for introducing the contents C or the components $C_1$, $C_2$, ... of the contents C and for draining the contents C, or for accessing different elements of the mixing vessel 1 that should be accessible for use, including the motor means 9, the pipes, pockets, tanks 5b and 6b, and the other elements.

The lower portion 3a of the wall 3 of the container 2 rests on the bottom wall 19, while the side portion 3b of the wall 3 of the container 2 is applied, when the container 2 is filled with its contents, against the peripheral wall 20.

If necessary, the external rigid holding device 18 also comprises, or forms, a housing or secondary space 22 that is located below the bottom wall 19. This housing or secondary space 22 enables the housing and the protection of the means of the mixing vessel 1 that is located below the container 2. It involves, for example, the pipe, the pocket or the tank 6b associated with the drain and, if necessary, the drive motor means 9 of the mixing means 7 when this drive motor means 9 is provided in the lower portion. If necessary, the housing or secondary space 22 can be formed inside an underframe 22a, such that the lower portion 3a of the wall 3 of the container 2, as well as the bottom wall 19 of the external rigid holding device 18, is separated from the ground or the support surface receiving the mixing vessel 1, whereby the latter is held in vertical position while allowing access to the drain opening 6a and, if necessary, the motor means 9.

If necessary, the external rigid holding device 18 also comprises heating means designed to heat the contents of the container 2. In this case, the flexible container is made of a material that has a certain thermal conductivity such that the implementation of the heating means in question allows the heating of the contents. In this case, and if necessary, means for monitoring the temperature of the contents in the container 2 and means for controlling the heating means are also provided. Such means for monitoring the temperature are carried by one or more ports 23 provided for this purpose.

If necessary, the external rigid holding device 18 also comprises doors, windows, etc. 18a.

According to one embodiment, the bottom wall 19 has the shape of a rounded cap, for example hemispherical or pseudo-hemispherical, whereby the lower portion 3a of the wall 3 of the container 2 has the same shape. This structural arrangement, combined with previously disclosed structural arrangements, contributes to the effectiveness of the mixing and the aeration.

The flexible container 2 can be found in three extreme states:
A disassembled state, in which the container 2 is disassembled from the external rigid holding device 18. In this state, the container 2, which is flexible in its entirety, can—when it is empty of contents C—be arranged in a manner flattened on itself. This state is most particularly useful for storage or shipping.
An empty assembled state, in which the container 2 is assembled in the external rigid holding device 18, as it was described above, the container 2 being empty of the contents C. In this state, the container 2 is arranged in the primary housing of the holding device 18 by resting on the bottom wall 19.
And finally, a filled assembled state, in which the container is assembled in the external rigid holding device 18, as it was described above, the container 2 being filled with the contents C. In this state, the container 2 is arranged in the primary housing of the holding device 18 by resting on the bottom wall 19 and by being applied against the peripheral wall 20.

For the process of implementing a mixing vessel 1 as it was just described, such a mixing vessel 1 whose drain port 6 is sealed is available, and the contents C or the components $C_1$, $C_2$, ... of the contents C are available.

These contents C or these components $C_1$, $C_2$ ... of the contents C are designed to be received in the container of the mixing vessel 1, and then mixed by means of aeration.

According to the process, first the contents C or the components $C_1$, $C_2$ ... of the contents C are introduced into the container 2.

Then, the mixing means 7 are used to stir the contents of the container 2 located in the inside space 4.

Furthermore, the aeration means 13 are used to deliver a certain amount of aeration gas to the contents of the container 2 located in the inside space 4.

The stirring and the aeration are implemented at least partially simultaneously, and if necessary totally simultaneously.

As a result of the structural arrangements of the mixing vessel 1 and the implementation process, the bubbles of the aeration gas are dispensed from the at least one extended dispensing element 15a, and they are distributed into the contents C located in the inside space 4 by, on the one hand, a first distribution into the lower region of the inside space 4 that is adjacent to the lower portion 3a of the wall 3 of the container 2, by the at least one extended element 15a for dispensing distribution gas and, on the other hand, a second distribution by the at least one mixing element 10 in the entire inside space 4 of the container 2.

The process can be the object of several embodiments. Thus, it is first possible to introduce a component, components $C_i$ of the contents C, or a portion of the components $C_1$, $C_2$ ... of the contents C into the container 2, and then mixing means 7 and aeration means 13 are implemented so as to deliver a certain amount of aeration gas to the contents, and then the remaining components(s) $C_1$, $C_2$, ... of the contents C is/are introduced into the container.

With the mixing vessel 1 comprising, on the one hand, the flexible container 2, and, on the other hand, the external rigid holding device 18, it is possible to proceed as follows.

A start is made from a mixing vessel 1 whose container 2 is disassembled from the external rigid holding device 18 and whose container is empty of contents and arranged in a manner that is more or less flattened on itself.

Then, the container 2 is assembled in the external rigid holding device 18 by arranging it in the primary housing of the latter by resting on its bottom wall 19.

Finally, the contents C or the components $C_1$, $C_2$ ... of the contents C are then introduced into the container 2.

The remainder of the process is as described above.

In the case where, as described above, the external rigid holding device 18 also comprises or forms a housing or secondary space 22 located below the bottom wall 19, the process also comprises a preliminary stage in which the mixing vessel means 1 that are to be located there are arranged under the bottom wall 19, such as the pipe, the pocket or the tank 6b associated with the drain, and, if necessary, the drive motor means 9 of the mixing means 7 when this drive motor means 9 is provided in the lower portion.

The mixing vessel can be the object of several embodiments based on different variant embodiments of the mixing means 7, the combined drain/bearing port 6+11 and aeration means 13, whereby the different variants of these means 7 and 13 can, moreover, most often be combined with one another.

More especially, different variant embodiments of the mixing means 7 will now be described.

According to a first possible variant embodiment (FIGS. 2 and 3), the at least one shaft 8 of mixing means 7 works with a single bearing, namely the lower bearing 11. In this case, the shaft 8 comprises an upper free end 8b that is separated from the upper portion 3c of the wall 3 of the container 2, for example located approximately at mid-height of the container 2. With such a variant, the drive motor means 9 with rotation of the shaft 8 is located toward the lower portion 3a of the wall 3 of the container 2.

Figure 8:
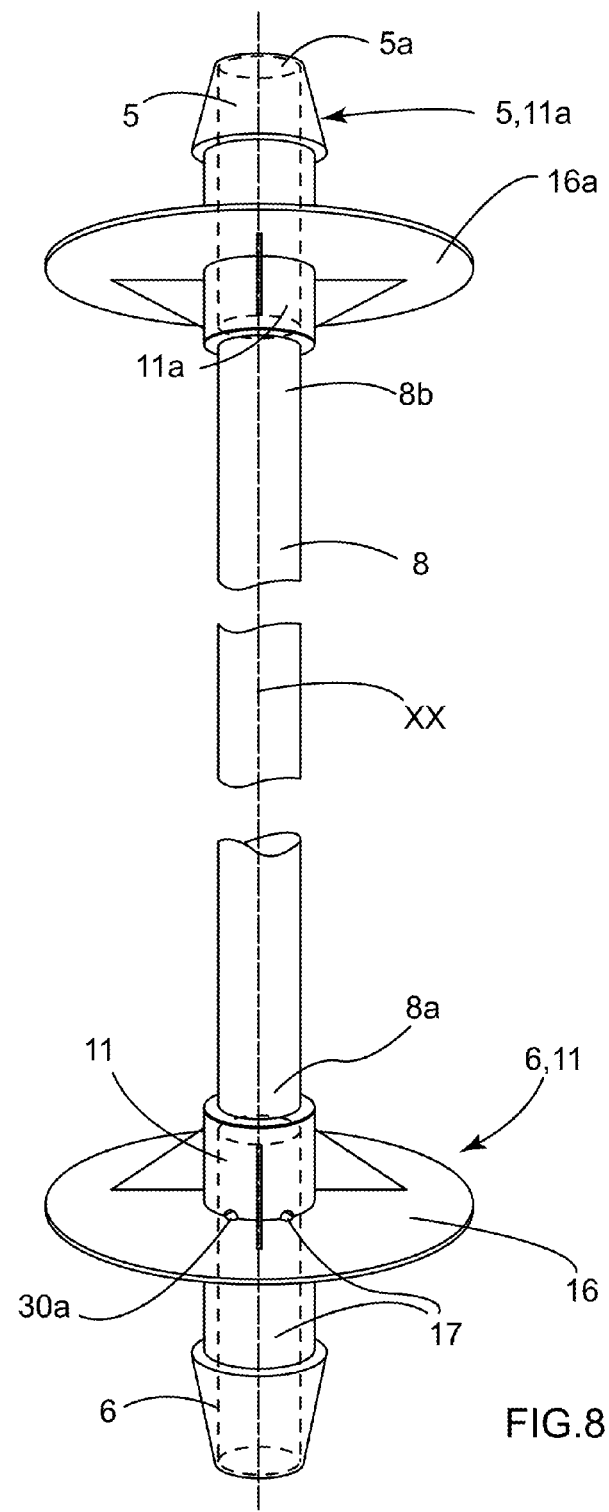
FIG. 8 is a perspective view of a unit that comprises a combined drain/bearing port and a combined introduction/bearing port.

According to a second possible variant embodiment (FIGS. 1 and 8), the at least one shaft 8 of the mixing means 7 works with two bearings. Its lower portion 8a works with the lower bearing 11, while its upper end portion 8b works with an upper bearing 11a that is adjacent to the upper portion 3c.

In this second variant, the upper bearing 11a preferably has a rigid flange 16a that is fixed rigidly to the upper portion 3c of the wall 3 of the container 2. From the inside, this flange 16a supports the upper bearing 11a that is located in the inside space 4.

According to a particular embodiment of the second variant (FIG. 8), the mixing vessel 1 also comprises at least one combined introduction/upper bearing port 5+11a that has the rigid flange 16a that was the device in question, which has a structure that is analogous to that of the flange 16 of the combined drain/lower bearing port 6+11.

In this case, this flange 16a is first provided with a passage for introducing the contents C or the components $C_1$, $C_2$, ... of the contents C, whereby this passage is in fluid communication on one side with the inside space 4 and on the other side with the outside of the container 2.

Second, this flange 16a is attached in a rigid and tight manner to the upper portion 3c of the wall 3 of the container 2 around the introduction opening 5a, whereby the introduction passage and the introduction opening 5a are in fluid communication.

Third, this flange 16a supports—on the inside—the upper bearing 11a that is located in the inside space 4 by being adjacent to the introduction passage without preventing the fluid communication between the introduction passage and the introduction opening 5a.

According to other possible variant embodiments, the drive motor means 9 with rotation of the shaft 8 is located toward the lower portion 3a (FIG. 2) or toward the upper portion 3c (FIG. 1) of the wall 3 of the container 2. If necessary, a motor means 9 is provided toward the lower portion 3a and toward the upper portion 3c. If the shaft 8 does not reach the upper portion 3c, the motor means 9 is arranged toward the lower portion 3a. If the shaft 8 reaches the upper portion 3c, the motor means 9 is arranged, as appropriate, toward the lower portion 3a or toward the upper portion 3c, or toward both.

According to another first possible variant embodiment (FIGS. 1, 2, 3, 9A, 9B, 10, 11A and 11B), the at least one shaft 8 of the mixing means 7 is located in its entirety in the inside space 4. In this case, the drive motor means 9 with rotation of the shaft 8—here toward the upper portion 3c of the wall 3 of the container 2—operates magnetically. For this purpose, a driving rotary disk 9a with magnetic poles (9b) (magnets), located outside of the container 2, operationally working with a driven rotary disk 24 with magnetic poles (24a), attached to the at least one shaft 8 with magnetic proximity of the driving rotary disk 9a, is provided.

Figure 9A:
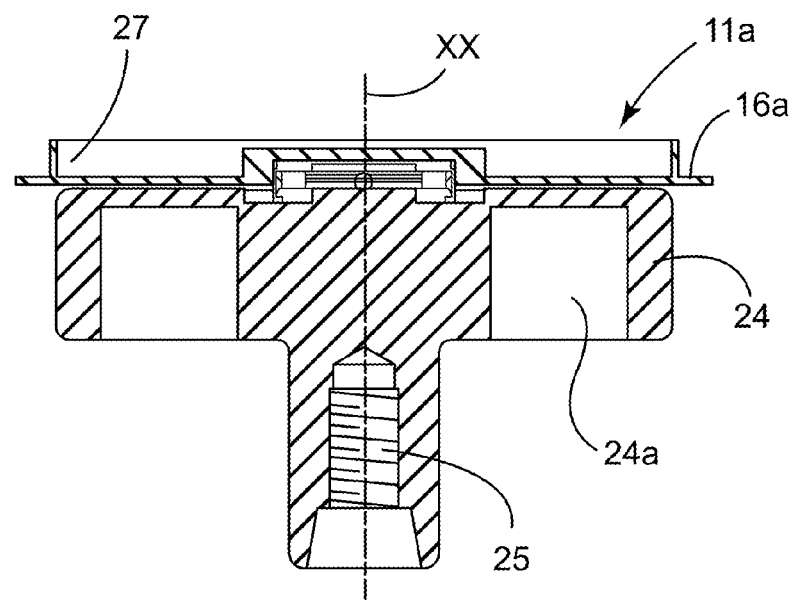
FIG. 9A is a diagrammatic cutaway view of the upper flange and magnetic drive means of the shaft of the mixing means.
Figure 9B:
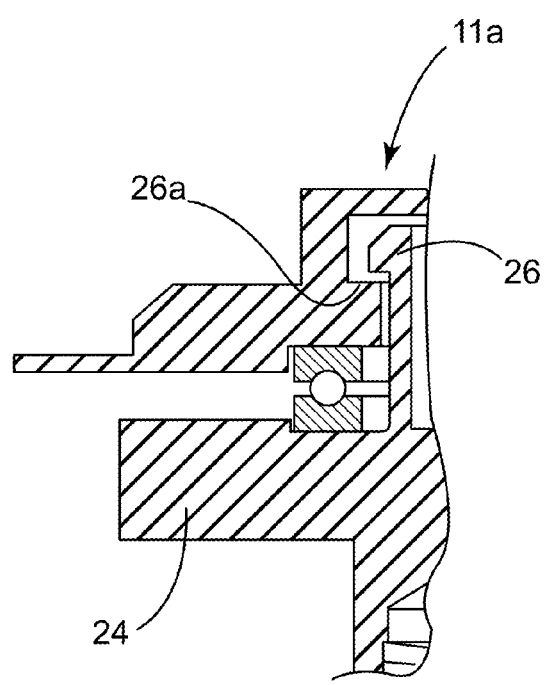
FIG. 9B is an enlarged cutaway view of an embodiment for connection between the upper flange and the magnetic drive means of the shaft.

Reference is now made more especially to FIGS. 9A and 9B.

The upper end 8b of the shaft 8 incorporates a magnetic disk 24 that includes a large number of magnets 24a and that is integrated by any means of attachment or design. The magnetic disk 24 is then positioned close to the upper flange 16a. The magnetic disk 24 is connected to the upper flange 16a so as to enable the magnetic motor means 9 (not shown) to act on the magnets 24a of the magnetic disk 24 within the width of the upper flange 16a.

According to FIG. 9A, the magnetic disk 24 is attached to the shaft 8 by screwing a threaded end of the shaft 8 into a threaded opening 25 inside the magnetic disk 24. Other means, such as cottered, adhesive, or attached elements, quick attachments, pins, screws, bolts, welding, or the like, as well as the formation of the magnetic disk 24 on the shaft 8 during its production, can be used to attach the magnetic disk 24 to the shaft 8, without limitation.

To hold the magnetic disk 24 in proper relationship with the upper flange 16a, a hook or a pawl 26 is provided on the magnetic disk 24, which is engaged on a lip 26a of the upper flange 16a. The particular attachment means of the magnetic disk 24 and the upper flange 16a consisting in the use of the pawl 26 combined with the upper flange 16a and the lip 26a combined with the magnetic disk 24 are not exclusive of others, alternatives such as quick attachments, sections and the like being possible, as soon as the magnetic disk 24 can rotate relatively freely relative to the upper flange 16a.

In addition, to ensure that the magnetic motor means 9 (not shown) preserves proper alignment with the magnets 24a of the magnetic disk 24, the upper flange 16a includes, in the embodiment shown, a drive coupling 27 that extends upward, starting from the outside surface of the upper flange 16a.

Figure 10:
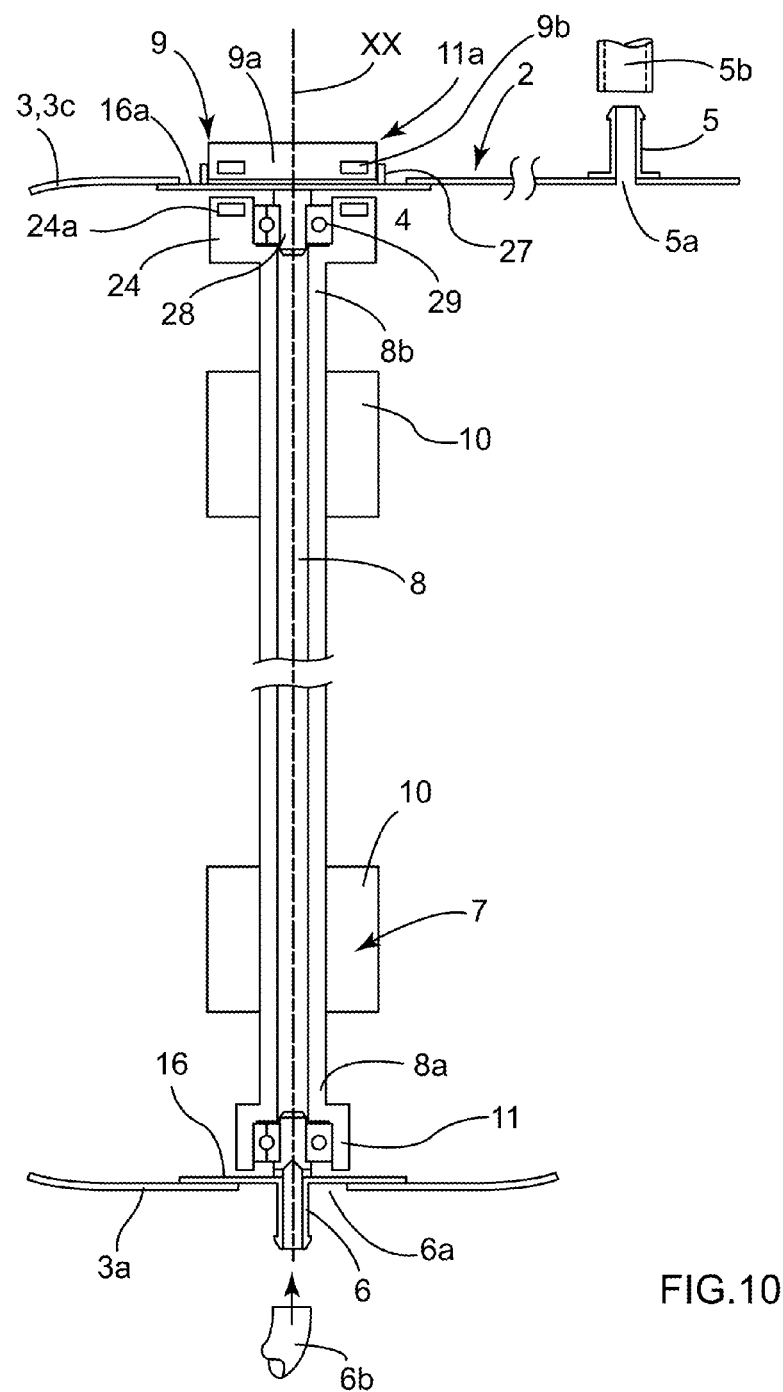
FIG. 10 is a partial axial cutaway view of another embodiment of a mixing vessel.
Figure 11A:
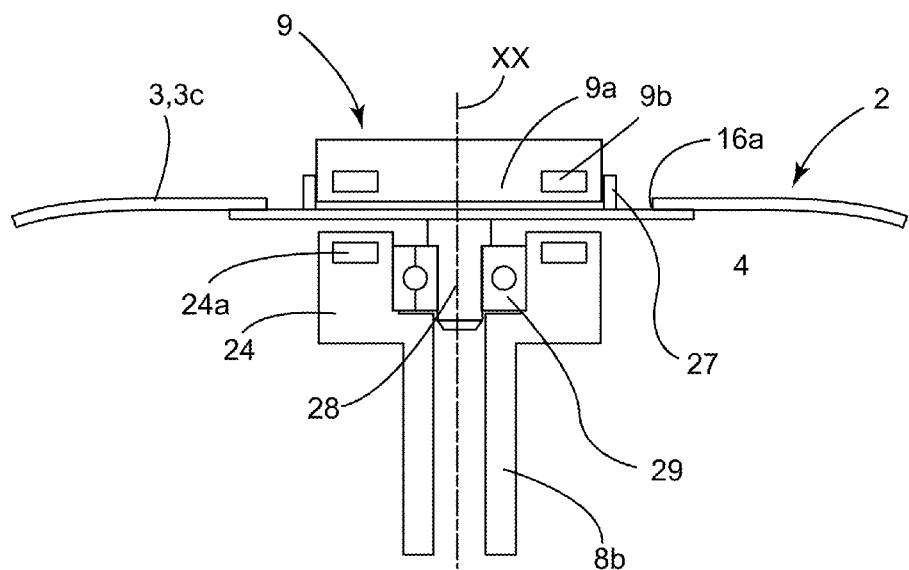
FIG. 11A is a partial cutaway view of the region of the upper flange of the embodiment illustrated in FIG. 10.
Figure 11B:
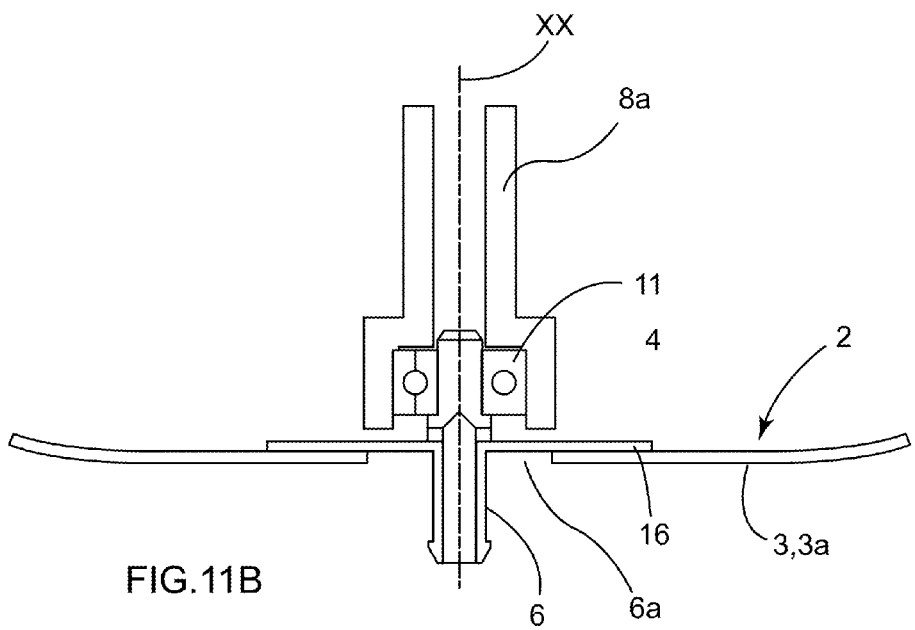
FIG. 11B is a partial cutaway of the region of the lower flange of the embodiment that is illustrated in FIG. 10.
Figure 12:
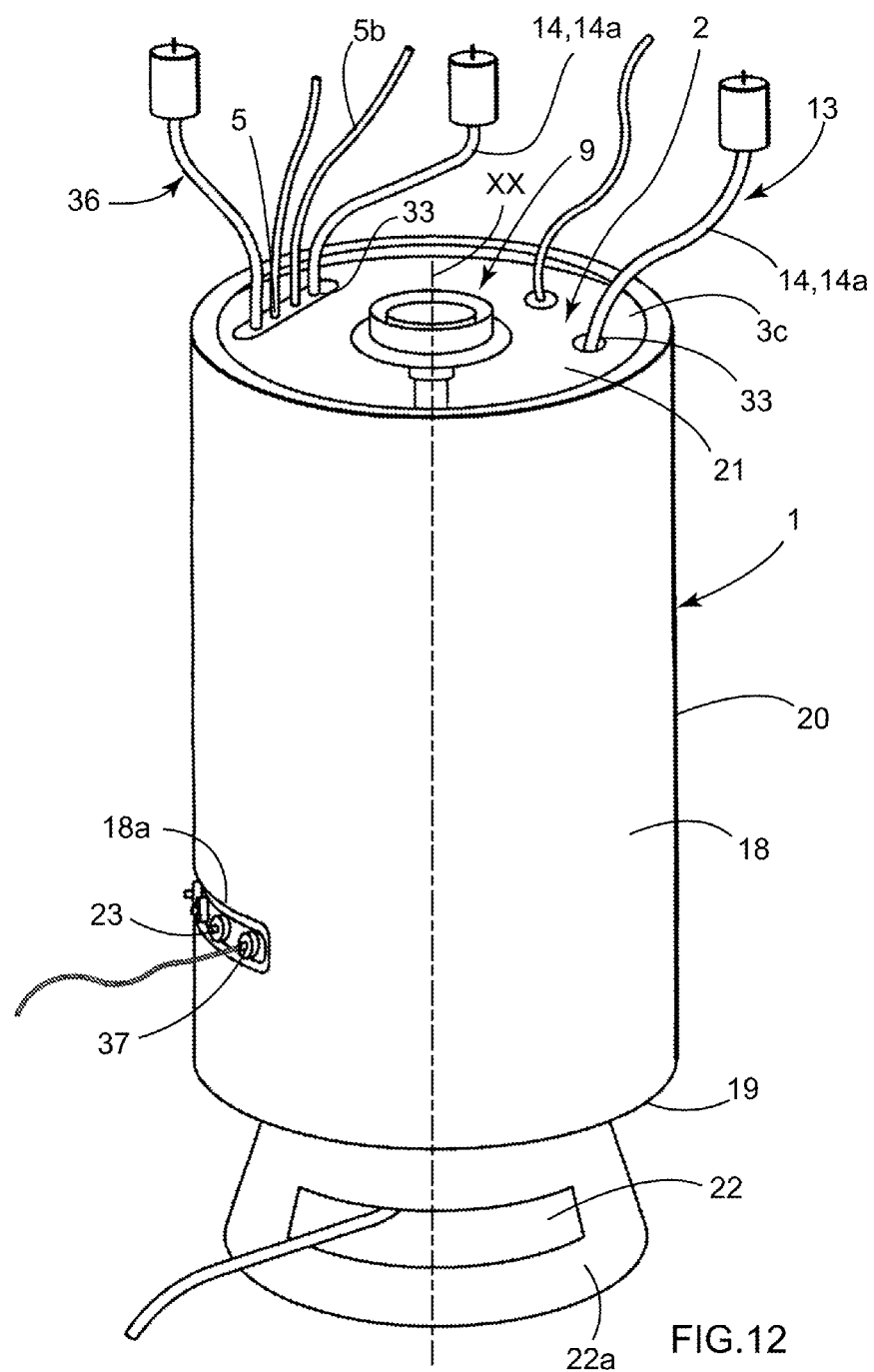
FIG. 12 is an external perspective view of the mixing vessel that shows the external rigid holding device.

Reference is now made more especially to FIGS. 10 and 11A.

The upper flange 16a is combined with a magnetic motor means 9, positioned inside the drive coupling 27, so as to orient the drive magnets 9b toward the driven magnets 24a. A pivot 28 is provided on the inside surface of the upper flange 16a for holding the shaft 8 at its upper end 8b, allowing its pivoting. Stop bearings 29 that are oriented vertically between the pivot 28 of the upper flange 16a and the upper end 8b of the shaft 8 are also provided. In addition, the magnetic disk 24 of this embodiment is formed on the terminal upper end 8b of the shaft 8 so as to be able to constitute a shaft 8 in a single piece, if this is desired.

According to another possible second variant embodiment (not shown), the at least one shaft 8 of the mixing means 7 is partially located in the interior space 4 and partially on the outside of the container 2, a sealed rotating connection being provided. In this case, the drive motor means 9 with rotation of the shaft 8 can have a mechanical operation, a driving rotary shaft, located on the outside of the container 2, operationally working with the outside portion of at least one shaft 8.

According to another first variant embodiment (FIGS. 1 and 2), the mixing means 7 comprise a single straightened shaft 8. "Straightened" is defined as the fact that the shaft 8 generally extends in a top-bottom or vertical direction.

According to another second variant embodiment (FIG. 3), the mixing means 7 comprise several—here, three—straightened shafts $8_\alpha$, $8_\beta$ and $8_\gamma$, with axes that are essentially parallel to one another and all adjoining the lower portion 3a of the wall 3 of the container 2. These shafts $8_\alpha$, $8_\beta$ and $8_\gamma$ are each able to drive in rotation at least one mixing element 10. The mixing vessel 1 comprises several mixing elements $10_\alpha$, $10_\beta$ and $10_\gamma$ in this variant embodiment.

According to another first variant (FIGS. 1 and 2), a shaft 8 of the mixing means 7 supports and drives a single mixing element 10 that is located in a single axial location on the shaft 8.

According to another second variant (FIG. 3), a shaft 8 of the mixing means 7—here, the shaft $8_\alpha$—supports and drives several mixing elements $10_\delta$ and $10_\epsilon$ located at a large number of axial locations on the shaft 8, $8_\alpha$.

A mixing element 10 can come in the form of a propeller having a hub that supports several blades.

As has been stated above, a mixing element 10 is spaced essentially from the lower portion 3a of the wall 3 of the container 2, from the lower bearing 11, and from at least one extended dispensing element 15a. According to one embodiment, this spacing or distance is on the order of at least one-quarter of the spacing between the lower portion 3a and the upper portion 3c of the wall 3 of the container 2. In particular, this spacing or distance is on the order of at least one-third of the spacing between the lower portion 3a and the upper portion 3c of the wall 3 of the container 2.

Now, more especially, different variant embodiments of the combined drain/bearing port 6+11 will be described.

Figure 7D:
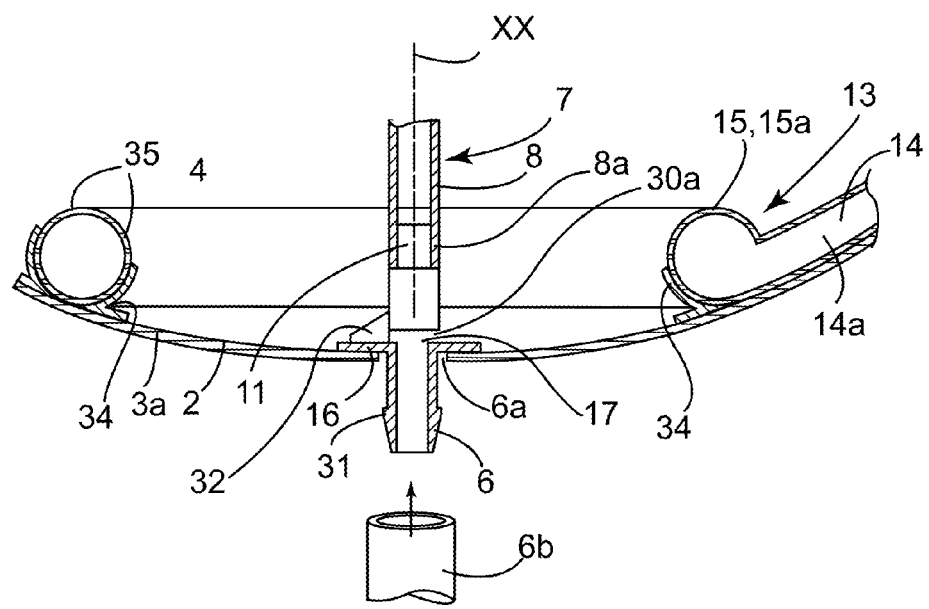
FIG. 7D is a partial sectional view that shows a combined drain/bearing port in operation in a container that is shown partially, and aeration means.

The lower flange 16 that is associated with the lower portion 8a of the shaft 8 and that is part of the mixing vessel 1 is more particularly shown in the FIGS. 7A, 7B and 7C according to several variant embodiments. In each of these variants, the lower flange 16 is formed by an essentially rigid material, preferably a rigid plastic material, in the form of a wall or small plate connected to the flexible container 2 in its XX axis, in the center of the lower portion 3a, which is the lowest portion of the container 2 whose shape is uncurved, as it has been said. This flange 16 can be connected to the flexible container 2 in any suitable manner so as to form a rigid and hermetic seal between the respective materials, rigid and flexible.

The upper portion of the lower flange 16, which is located in the inside space 4 of the container 2, includes the lower bearing 11 that forms a connecting means that works with the lower portion 8a of the shaft 8.

The bearing 11 can be a male bearing in the form of a journal, as shown in FIGS. 7A and 7B, inserted in an open cavity formed in the lower portion 8a of the shaft 8. The bearing 11 can be a female bearing in the form of a ring, as shown in FIG. 7C, in the cavity of which is inserted the lower portion 8a of the shaft 8.

It is preferred that the shaft 8 adapt to the bearing 11 with minimal friction, such that the shaft 8 can rotate freely on the bearing 11. For this purpose, provisions are made possibly to include a stop bearing (not shown) between the lower portion 8a of the shaft 8 and the bearing 11, or plain bearings, ball bearings or roller bearings can be provided.

If this is desired, a pawl (not shown), which does not significantly compromise the rotation of the shaft 8 on the bearing 11, can be provided so as to hold the shaft 8 on the bearing 11.

It is understood that the lower bearing 11 and the upper bearing 11a, when provided, can have structures that are analogous to those more especially described above. As indicated, as appropriate, the upper bearing 11a ensures only the bearing function or else it is combined in an introduction/bearing port 5/11a.

As has been indicated, a drain port 6 with a drain opening 6a formed in the container 2 is associated with the lower flange 16. The flange 16 is therefore provided with a drain passage 17 in fluid communication on one side with the inside space 4 of the container 2 and on the other side with the outside of the container 2 via the drain port 6 itself, here in the shape of a tube section that comprises an end portion comprising an exterior peripheral projection in the form of a shark's tooth, enabling the attachment of the end portion of a drain pipe 6b.

The drain passage 17 comprises one or more openings 30a that ensure the communication with the inside space 4. These openings 30a are arranged based on the structure of the bearing 11.

In the variant of FIG. 7A, a large number of radial or essentially radial openings 30a, formed at the base of the bearing 11 in the form of a journal, distributed all around, are provided, and these openings 30a empty into the drain port 6.

In the variant of FIG. 7B, a single, axial opening 30a, made axially below the base of the bearing in the form of a journal 11, which base is raised relative to the flange 16 by means of brackets 32 arranged radially and axially, is provided, a space thus being made between this base and the flange 16.

In the variant of FIG. 7C, a large number of radial or essentially radial openings 30a, made at the base of the bearing 11 in the form of a ring, distributed all around, are provided, and these openings 30a empty into the drain port 6.

Now, different variant embodiments of the aeration means 13 will be described more especially.

The at least one tubular aeration gas intake element 14a extends into the inside space 4 of the container by being held essentially adjoining or adjacent to or against the inside surface of the wall 3 of the container 2 so as to prevent the tubular element 14a from diverging in the container, whereas the contents of the latter are stirred by the mixing means 7 at the risk of interfering with the latter.

Figure 2:
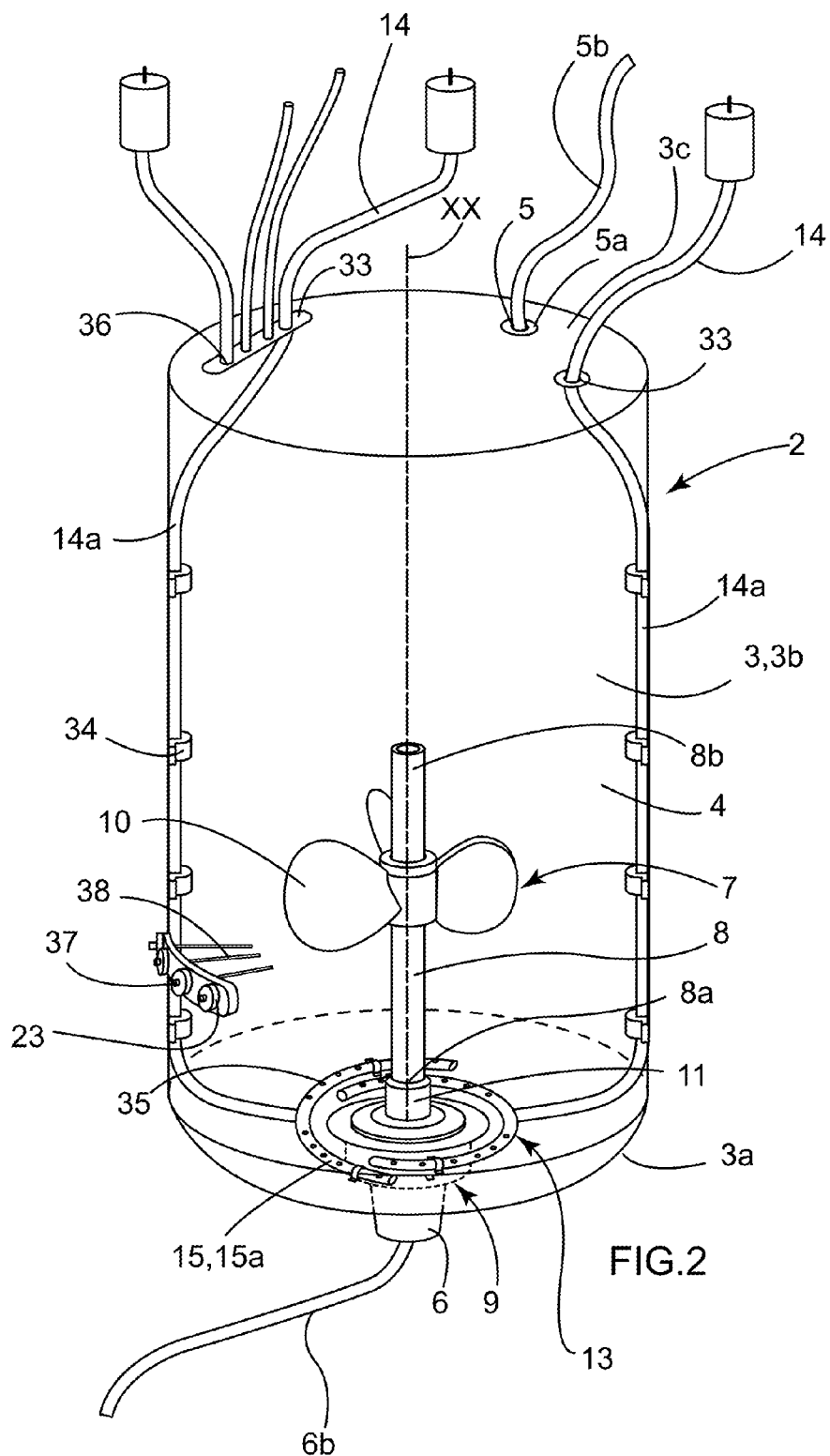
FIG. 2 is a view that is analogous to FIG. 1 of another possible embodiment of a mixing vessel.
Figure 3:
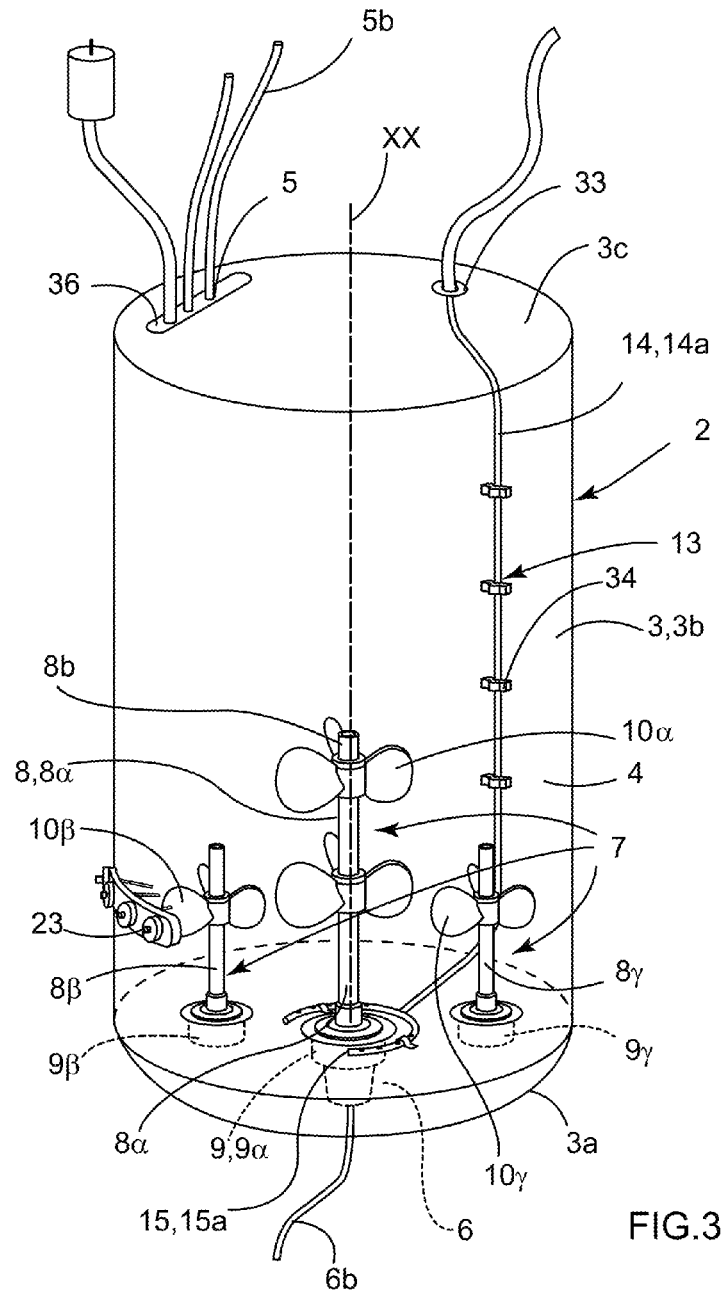
FIG. 3 is a view that is analogous to the preceding views of another possible embodiment of a mixing vessel.
Figure 4:
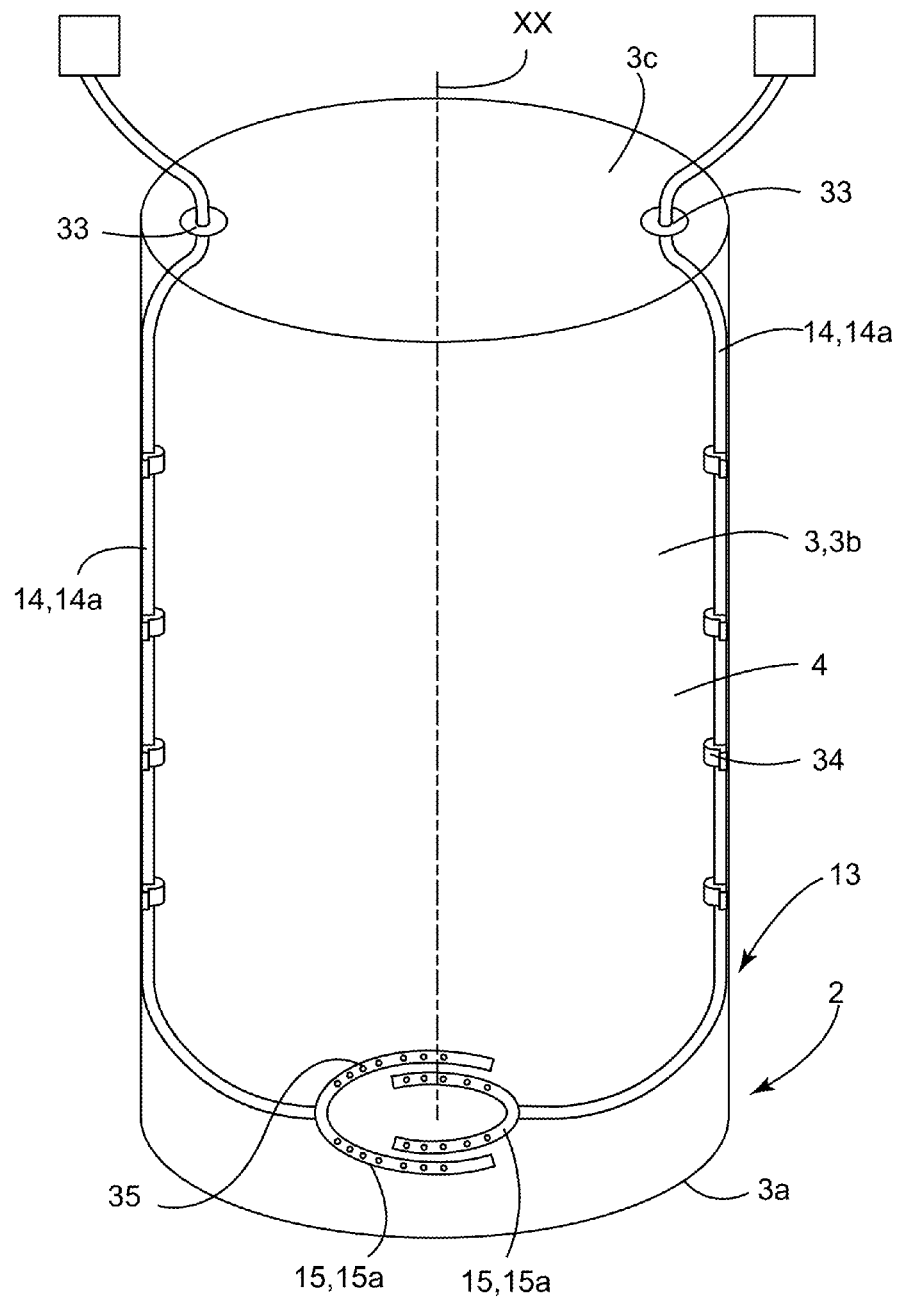
FIG. 4 is a view that is analogous to the preceding views of another possible embodiment of a mixing vessel.
Figure 5:
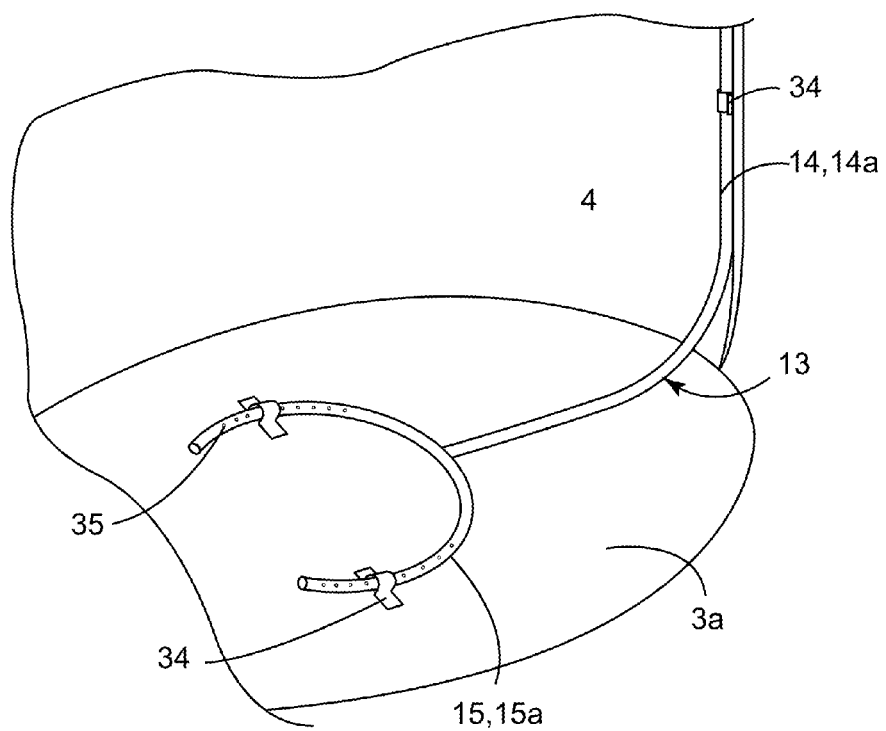
FIG. 5 is a partial perspective view of the aeration means of a mixing vessel.
Figure 6:
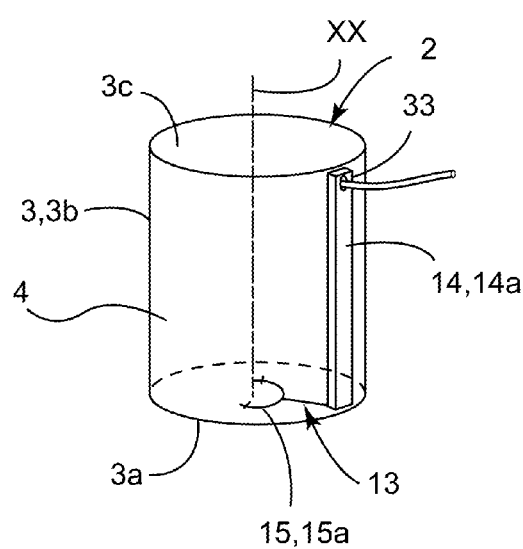
FIG. 6 is a partial perspective view of the aeration means of a mixing vessel with intake means in sleeve form.

For this purpose, according to the different variant embodiments that can be considered, the at least one tubular aeration gas intake element 14a is at least partially structurally separate from the wall 3 of the container 2 and held to it by gluing, welding, or by means of holding parts 34, provided as shown in FIGS. 1 to 3, and/or at least partially structurally an integral part of the wall 3 of the container 2 as is shown in FIG. 6.

With reference to FIGS. 1 to 3, typical examples of the holding parts 34 are adhesive strips, flanges, tabs or the like that are arranged from place to place along the tubular aeration gas intake element 14a.

With reference to FIG. 6, the tubular intake element 14a is provided with a sleeve here. This sleeve is constructed from a length of material that is preferably identical to that from the inside surface of the wall 3 of the flexible container 2, welded or otherwise attached on its longitudinal sides to the inside surface of the wall 3 by being arranged on the inside of the flexible container 2. The tubular region that is encompassed between this sleeve and the inside surface of the wall 3 of the flexible container 2 channels the gas from the outside of the mixing vessel to the aeration gas dispensing means 15.

Upstream (intake of the aeration gas), the at least one tubular aeration gas intake element 14a passes through the wall 3 of the container into the upper portion 3c by a tight connection 33. This structural arrangement makes it possible, on the one hand, to release the region that is located below the lower portion 3a that is not encumbered by this tubular element 14a, and, on the other hand, to not be obligated to provide a passage opening for the tubular element 14a in the lower portion 3a of the wall 3 of the container 2.

In contrast, the at least one extended element 15a for dispensing aeration gas is held adjoining or adjacent to the inside surface of the lower portion 3a of the wall 3 of the container 2.

According to the different variant embodiments that can be considered, the at least one extended element 15a for dispensing aeration gas is, at least in part, structurally separate from the wall 3 of the container 2 and held to it by gluing, welding or by means of connected holding parts and/or at least partially structurally an integral part of the wall 3 of the container 2. In any case, the at least one extended element 15a for dispensing aeration gas does not pass through the wall 3 of the container 2. Such connected holding parts, when they are provided, can be identical or analogous to those used for the tubular intake element 14a.

Of course, the variant embodiment of the at least one tubular aeration gas intake element 14a complies with that of at least one extended element 15a for dispensing aeration gas.

The at least one tubular aeration gas intake element 14a extends, from upstream to downstream, from the outside to the inside of the container 2 and the extended element 15a for dispensing aeration gas, by the tight connection 33 in the upper portion 3c, then axially along the inside surface of the side portion 3b up to the inside surface of the lower portion 3a, and then radially or essentially radially on the inside surface of the lower portion 3a, to the at least one extended element 15a for dispensing aeration gas that adjoins or is adjacent to the same inside surface of the lower portion 3a of the wall 3.

The at least one extended element 15a for dispensing aeration gas is of the type that comprises a wall that is provided with a large number of holes 35, distributed on this wall. The tubular aeration gas intake element 14a empties in fluid communication on one side of this wall 15a, whereas the other side of this wall 15a is located in the inside space 4. The holes 35 can allow the passage of the bubbles of aeration gas coming from the intake means 14 toward the inside space 4.

The holes 35 can be the subject of different variant embodiments.

According to one possible variant embodiment, the holes 35 of the large number of holes 35 are oriented with different axes of inclination on the vertical XX axis.

According to other possible variant embodiments, the holes 35 of the large number of holes 35 are either the same size or different sizes.

Thus, the flow rate of the aeration gas exiting from the holes 35 and the discharge orientation of the gas bubbles downstream from the wall of the extended element 15a for dispensing aeration gas can be adapted based on requirements.

These variant embodiments apply to a variant embodiment according to which the aeration means 13 comprise a single unit of aeration gas intake means 14 and means 15 for dispensing aeration gas (not shown) as well as to a variant according to which the aeration means 13 comprise several separate units of intake means 14 of one or more aeration gases and means 15 for dispensing the aeration gas(es), as it is shown in FIGS. 1, 2, 3 and 4.

Such a structural arrangement with several separate units of intake means 14 and means 15 for dispensing one or more aeration gases is particularly well suited to the case where the process requires aeration with several gases, for example the aeration with oxygen and aeration with carbon dioxide.

In the case of an arrangement with several separate units of intake means 14 and means 15 for dispensing one or more aeration gases, the different means 15 for dispensing the large number of dispensing means 15 have either the same characteristics or have different characteristics that are associated with the type or the volume of gas introduced into the contents C. These different characteristics can include, but in a non-limiting way, the size and the number of holes 35. According to a variant embodiment, the aeration means 13 are such that a single extended dispensing element 15a is associated with a single tubular intake element 14a. According to other variant embodiments, several extended dispensing elements 15a are associated with a single tubular intake element 14a, or conversely, a single extended dispensing element 15a is associated with several tubular intake elements 14a.

The at least one extended element 15a for dispensing aeration gas can be the object of different variant embodiments.

In one variant embodiment, the at least one extended element 15a for dispensing aeration gas has, in elevation, a general annular or pseudo-annular shape, which has, in a transverse straight cross-section, a general shape that can be circular or pseudo-circular, or elliptical or pseudo-elliptical. At least one such annular element 15a is in fluid communication with the tubular intake element 14a.

According to one variant, at least one particularly radial transverse element is associated with the annular element 15a, which makes possible a more distributed dispensing of gas.

As appropriate, the annular element 15a is in the shape of a complete ring that is closed on itself, in circular fluid communication that may or may not be continuous, or is in the shape of an incomplete ring that is open relative to itself. In one embodiment, the angular opening of such an open ring is between about 180° and 270°.

In one variant embodiment, such an annular element 15a is essentially centered on the combined drain/bearing port.

In one variant embodiment, the aeration means 13 comprise a single unit of aeration gas intake means 14 and means 15 for dispensing aeration gas. In another variant embodiment, the aeration means 13 comprise several separate units of intake means 14 of one or more aeration gases and means 15 for dispensing the aeration gas(es).

Such a unit 14+15 of aeration means 13 can be the object of different variant embodiments in that said unit comprises either a single tubular aeration gas intake element 14*a* that communicates with a single annular element 15*a* for dispensing aeration gas, or a single tubular element 14*a* that communicates with several annular elements 15*a*, or several tubular elements 14*a* that communicate with a single annular element 15*a*, or else several tubular elements 14*a* that communicate with several annular extended elements 15*a*.

In contrast, in the case where such a unit 14+15 comprises several annular elements 15*a* for dispensing separate aeration gases, it is possible, in a variant embodiment, that these—or some of these—annular elements 15*a* are located in several radial locations in the inside space 4 and toward the lower portion 3*a* of the wall 3 of the container 2. In this case, such radial locations can, in a variant embodiment, be spaced essentially radially from one another relative to the XX axis between the drain/bearing port 6+11 to the vicinity of the side portion 3*b* of the wall 3 of the container 2.

With such an arrangement, the aeration is particularly well distributed upon its dispensation.

As has been stated above, an annular element 15*a* for dispensing aeration gas is spaced essentially radially from the drain/bearing port 6+11. According to one embodiment, this spacing or distance is on the order of at least one-fifth of the diameter of the lower portion of the wall 3 of the container 2.

At least one aeration gas drain port 36 that works with at least one drain opening made in the upper portion 3*c* of the wall 3 of the container 2 can be associated operationally with aeration means 13 that were just described. Such an aeration gas drain port 36 can be provided with a non-return valve, preventing the introduction into the container 2 of fluids or contaminants that are not desired or are undesirable. Such an aeration gas drain port 36 makes it possible to drain the gas that has not been mixed into the contents of the container 2 from the container 2 toward the outside. Such an aeration gas drain port 36 can be in fluid communication with the aeration gas intake for the purpose of recycling.

The mixing vessel 1 can, in certain embodiments, also comprise one or more assembly ports 37 for example for an operational means, able to ensure the holding of an operational element 38 such as typically the collection or the measurement of data and sampling for purposes of analysis.

The invention claimed is:

1. A mixing vessel (1) designed to receive biopharmaceutical contents (C) for mixing thereof, said mixing vessel comprising:
1) a flexible container (2), comprising:
 i) a wall (3) that has a lower portion (3*a*), a side portion (3*b*), and an upper portion (3*c*), the wall delimiting an inside space (4) that receives a certain amount of the biopharmaceutical contents (C), the wall having introduction openings (5*a*) and a drain opening (6*a*), and
 ii) one or more ports (5), at corresponding one of more of the introduction openings (5*a*), the one or more ports (5) located to introduce the contents (C) or components of the contents (C) into the container (2);
2) a mixing unit (7), the mixing unit (7) comprising:
 i) a motor (9),
 ii) at least one mixing element (10) located within the inside space (4) delimited by the wall (3), wherein when driven in rotation, the at least one mixing element (10) mixes the contents (C) within the inside space (4), and
 iii) at least one shaft (8) operatively connected to the motor (9) and the at least one mixing element (10), the shaft (8) driven in rotation by motor (9) and driving in rotation the at least one mixing element (10);
3) an aeration means (13) arranged and configured to deliver to the contents (C) a certain amount of aeration gas, the aeration means (13) comprising:
 i) a dispensing means (15) that dispenses aeration gas, the dispensing means comprising at least one extended dispensing element (15*a*) with a wall that allows passage of bubbles of aeration gas, the dispensing element being located in the inside space (4) toward the lower portion (3*a*) of the wall (3) of the container (2), and
 ii) an aeration gas intake means (14) having at least one tubular aeration gas intake element (14*a*) that extends in fluid communication from an outside of the container (2) to the at least one extended dispensing element (15*a*) of the dispensing means (15), and
4) a combined contents drain and lower bearing port, located at the drain opening (6*a*) adjacent to the lower portion (3*a*) of the wall (3) of the container (2), and operatively connected to work with a lower portion (8*a*) of the shaft (8), wherein the combined contents drain and lower bearing port comprises a flange (16), the flange (16) provided with a drain passage (17) in fluid communication on a first side within the inside space (4) and on an opposite second side with the outside of the container (2), wherein the flange (16) is attached to the lower portion (3*a*) of the wall (3) of the container (2) around the drain opening (6*a*) with the drain passage (17) and the drain opening (6*a*) in fluid communication therebetween, and an upper portion of the flange (16) includes a lower bearing (11) within the inside space (4), adjacent to the drain passage (17) without preventing the fluid communication between the drain passage (17) and the drain opening (6*a*),
wherein the at least one extended dispensing element (15*a*) is spaced radially around the combined contents drain and lower port,
wherein the at least one tubular aeration gas intake means (14) extends from the at least one extended dispensing element (15*a*), in the inside space (4), along an inside surface of the lower portion (3*a*) and the side portion (3*b*) of the wall (3) of the container (2) and extends to the outside of the container (2) from, or from a vicinity of, the upper portion (3*c*) of the wall (3) of the container (2),
wherein the at least one mixing element (10) is spaced from the lower portion (3*a*) of the wall (3) of the container (2), from the lower bearing (11), and from at least one extended element (15*a*), and
wherein, in operation of the mixing vessel, the bubbles of the aeration gas dispensed from the at least one extended dispensing element (15*a*) are distributed in the contents (C) by a first distribution in a lower region of the inside space (4) that is adjacent to the lower portion (3*a*) of the wall (3) of the container (2), by the at least one extended dispensing element (15*a*) and by a second distribution by the at least one mixing element (10) in an entirety of the inside space (4) of the container (2).

2. The mixing vessel (1) according to claim 1, further comprising an upper bearing (11*a*) that works with an upper portion of the at least one shaft (8).

3. The mixing vessel (1) according to claim 2, further comprising:
at least one combined introduction and upper bearing port that has a flange (16*a*):
provided with a passage that allows introduction of the contents (C) or the components of the contents (C) in fluid communication on one side with the lower space (4), and on the other side with the outside of the container (2), attached to the upper portion of the wall (3) of the container (2) around the introduction opening, whereby the introduction passage and the introduction opening are in fluid communication, supporting from the inside the upper bearing (11a) that is located in the inside space (4), adjacent to the introduction passage without preventing the fluid communication between the introduction passage and the introduction opening.

4. The mixing vessel (1) according to claim 1, wherein the at least one shaft (8) of the mixing unit (7) is located in its entirety in the inside space (4), whereby the drive motor (9) with rotation of the shaft (8) operates magnetically, with a rotary disk driving with magnetic poles (9a), located on the outside of the container (2), operationally working with a rotary disk driven with magnetic poles, attached to the at least one shaft (8) with magnetic proximity of the driving rotary disk (9a).

5. The mixing vessel (1) according to claim 1, wherein the at least one shaft (8) of the mixing unit (7) is partially located in the inside space (4) and partially on the outside of the container (2), whereby the drive motor (9) with rotation of the shaft (8) operates mechanically, with a driving rotary shaft, located on the outside of the container (2), operationally working with the outside portion of the at least one shaft (8).

6. The mixing vessel (1) according to claim 1, wherein the mixing unit (7) comprise either a single straight shaft (8) or plural straight shafts (8) with parallel axes, each able to drive in rotation at least one mixing element (10).

7. The mixing vessel (1) according to claim 1, wherein the shaft (8) of the mixing unit (7) supports and drives either a single one of said at least one mixing element (10) that is located in a single axial location on the shaft (8) or plural of said at least one mixing element that are located in a plural number of axial locations on the shaft (8).

8. The mixing vessel (1) according to claim 1, wherein said at least one mixing element (10) is spaced from the lower portion (3a) of the wall (3) of the container (2), from the lower bearing (11), and from at least one extended dispensing element (15a), from a distance on the order of at least one-quarter of the spacing between the lower portion (3a) and the upper portion (3c) of the wall (3) of the container (2).

9. The mixing vessel (1) according to claim 1, wherein said at least one mixing element (10) is spaced from the lower portion (3a) of the wall (3) of the container (2), from the lower bearing (11), and from at least one extended dispensing element (15a), from a distance on the order of at least one-third of the spacing between the lower portion (3a) and the upper portion (3c) of the wall (3) of the container (2).

10. The mixing vessel (1) according to claim 1, wherein the at least one tubular aeration gas intake element (14a) extends in the inside space (4) by being held adjoining or adjacent to the inside surface of the wall (3) of the container (2).

11. The mixing vessel (1) according to claim 1, wherein the at least one tubular aeration gas intake element (14a) is
   i) at least partially structurally separate from the wall (3) of the container (2) and is also held to the wall (3) by gluing, welding, or by connected holding parts, or
   ii) is an integral part of the wall (3) of the container (2).

12. The mixing vessel (1) according to claim 1, wherein the at least one tubular aeration gas intake element (14a) passes through the wall (3) of the container (2) via a connection.

13. The mixing vessel (1) according to claim 1, wherein the at least one tubular aeration gas intake element (14a) passes through the wall (3) of the container (2) into the upper portion (3c).

14. The mixing vessel (1) according to claim 1, wherein the at least one extended element (15a) is held adjoining or adjacent to the inside surface of the lower portion (3a) of the wall (3) of the container (2).

15. The mixing vessel (1) according to claim 1, wherein the at least one extended element (15a) is held to the wall (3) by gluing, welding or by connected holding parts.

16. The mixing vessel (1) according to claim 1, wherein the at least one extended element (15a) is an integral part of the wall (3) of the container (2).

17. The mixing vessel (1) according to claim 1, wherein the at least one extended element (15a) does not pass through the wall (3) of the container (2).

18. The mixing vessel (1) according to claim 1, wherein the at least one extended element (15a) comprises a wall (3) that is provided with a plural number of distributed holes that can allow the passage of the bubbles of aeration gas coming from the aeration gas intake means (14).

19. The mixing vessel (1) according to claim 18, wherein the plural number of holes that can allow the passage of the bubbles of aeration gas coming from the aeration gas intake means (14) are oriented with different axes of inclination with respect to the vertical line.

20. The mixing vessel (1) according to claim 18, wherein the holes of the plural number of holes are either the same size or different sizes.

21. The mixing vessel (1) according to claim 1, wherein the at least one extended element (15a) has, in a transverse straight cross-section, a circular, or pseudo-circular, or elliptical or pseudo-elliptical shape.

22. The mixing vessel (1) according to claim 1, wherein the at least one extended element (15a) comprises at least
   i) one complete ring that is closed on itself, or
   ii) at least one incomplete ring that is open relative to itself, having an angular opening of between about 180° and 270°.

23. The mixing vessel (1) according to claim 1, wherein the aeration means (13) comprise a single unit of aeration gas intake means (14) and aeration gas dispensing means (15) or plural separate units of said intake element of one or more aeration gases and said dispensing means (15).

24. The mixing vessel (1) according to claim 23, wherein a unit of aeration means (13) comprises
   i) a single tubular aeration gas intake element (14a) that communicates with a single extended element (15a), or
   ii) a single tubular aeration gas intake element (14a) that communicates with plural of said extended element (15a), or
   iii) plural tubular aeration gas intake elements (14a) that communicate with a single extended element (15a), or
   iv) plural tubular aeration gas intake elements (14a) that communicate with plural of said extended element (15a).

25. The mixing vessel (1) according to claim 1, comprising plural of said extended element (15a), and wherein at least some of the plural extended elements (15a) are located in a plural number of radial locations in the inside space (4) toward the lower portion (3a) of the container (2), and are spaced radially from the combined contents drain and lower port to the vicinity of the side portion (3b) of the wall (3) of the container (2).

26. The mixing vessel (1) according to claim 1, wherein an extended element (15a) is spaced radially from the combined contents drain and lower port, from a distance on the order of at least one-fifth of the diameter of the lower portion (3a) of the wall (3) of the container (2).

27. The mixing vessel (1) according to claim 1, wherein only the drain (6), and the drive motor (9) of the mixing unit (7), projects under the lower portion (3a) of the wall (3) of the container (2).

28. The mixing vessel (1) according to claim 1, further comprising one or more gas drain ports working with at least one drain opening made in the upper portion of the wall (3) of the container (2), provided with a nonreturn valve, preventing the introduction into the container (2) of fluids or contaminants that are undesirable.

29. The mixing vessel (1) according to claim 1, wherein the container (2) has a capacity up to 5,000 liters.

30. The mixing vessel (1) according to claim 1, further comprising an external holding device (18) of the container (2), comprising a bottom wall (19), a peripheral wall (20), and an upper opening (21), delimiting a primary housing in which is arranged, in a removable way, the flexible container (2) whose lower portion rests on the bottom wall (19) and whose side position is applied, when the container (2) is filled with the contents (C), against the peripheral wall (20).

31. The mixing vessel (1) according to claim 30, wherein the external holding device (18) also comprises a secondary housing (22) below the bottom wall (19) housing and protecting the drain (6) and the drive motor (9) of the mixing unit (7) when it is provided in the lower portion.

32. The mixing vessel (1) according to claim 30, wherein the container (2) can be found in three extreme states:
  a disassembled state of the external holding device (18) in which the container (2) can be arranged flattened on itself,
  an assembled state of the external holding device (18) in which the container (2), empty of the contents (C), is arranged in the primary housing of the holding device (18) by resting on the bottom wall (19), and
  an assembled state of the external holding device (18) in which the container (2), filled with its contents (C), is arranged in the primary housing of the holding device (18) by resting on the bottom wall (19) and by being applied against the peripheral wall (20).

33. The mixing vessel (1) according to claim 1, wherein the vessel is configured for a bioreaction to be produced therein, the mixing vessel (1) being a bioreactor.

34. The mixing vessel (1) according to claim 1, wherein, the shaft (8) of the mixing unit (7) includes an upper portion (8b) that extends to and works with an upper bearing (11a) that is adjacent to the upper portion (3c) of the wall of the container (2),
  the motor (9) is located at the upper portion (3c) of the wall of the container (2), and
  said the at least one mixing element (10) is spaced from the lower portion (3a) of the wall (3) of the container (2), from the lower bearing (11), and from at least one extended dispensing element (15a), from a distance on the order of at least one-quarter of the spacing between the lower portion (3a) and the upper portion (3c) of the wall (3) of the container (2).

35. A process for using a mixing vessel (1) according to claim 1, wherein:
  such a mixing vessel (1) whose drain port (6) is sealed is available,
  the contents (C) or the components of the contents (C) designed to be received in the container (2) of the mixing vessel (1) and then mixed are available,
  the contents (C) or the components of the contents (C) are introduced into the container (2),
  the mixing unit (7) are used to stir the contents (C) of the container (2),
  the aeration means (13) are used to deliver to the contents (C) a certain amount of aeration gas, aeration and mixing being carried out at least partially simultaneously, and
  the aeration gas bubbles are dispensed from the at least one extended element (15a) for dispensing aeration gas, and they are distributed into the contents (C) for a first distribution in the lower region of the inside space (4) that is adjacent to the lower portion (3a) of the wall (3) of the container (2), by the at least one extended element (15a) for dispensing aeration gas and a second distribution by the at least one mixing element (10) in the entire inside space (4) of the container (2).

36. The process according to claim 35, wherein first, a component or a portion of the components of the contents (C) is introduced into the container (2), the mixing unit (7) and the aeration means (13) are used, and a certain amount of aeration gas is introduced to be delivered to the contents (C), and the remaining component(s) of the contents (C) is introduced into the container (2).

37. The process according to claim 35, wherein:
  a start is made from a mixing vessel (1) whose container (2) is disassembled from an external holding device (18), empty of contents (C), and arranged flattened upon itself,
  the container (2) is assembled with the external holding device (18) by arranging it in the primary housing of the latter and by resting on its bottom wall (19),
  the contents (C) or components of the contents (C) are then introduced into the container (2).

38. The process according to claim 35, wherein the drain (6) and the drive motor (9) of the mixing unit (7) are arranged under the lower portion (3a) of the wall (3) of the container (2) when it is provided in the lower portion.

\* \* \* \* \*